United States Patent
Sagi et al.

(10) Patent No.: US 9,764,008 B2
(45) Date of Patent: Sep. 19, 2017

(54) VARIANTS OF TACE PRO-DOMAIN AS TNF-A INHIBITOR AND THEIR MEDICAL USE

(71) Applicant: Yeda Research and Development Co. Ltd., Rehovot (IL)

(72) Inventors: Irit Sagi, Rehovot (IL); Eitan Wong, Rehovot (IL); Ran Afik, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 100 days.

(21) Appl. No.: 14/398,754

(22) PCT Filed: May 9, 2013

(86) PCT No.: PCT/IL2013/050400
§ 371 (c)(1),
(2) Date: Nov. 4, 2014

(87) PCT Pub. No.: WO2013/168164
PCT Pub. Date: Nov. 14, 2013

(65) Prior Publication Data
US 2015/0132281 A1    May 14, 2015

Related U.S. Application Data

(60) Provisional application No. 61/644,551, filed on May 9, 2012.

(51) Int. Cl.
*A61K 38/54*      (2006.01)
*A61K 38/48*      (2006.01)
*C12N 9/64*       (2006.01)

(52) U.S. Cl.
CPC ........ *A61K 38/4886* (2013.01); *C12N 9/6489* (2013.01); *C12Y 304/24086* (2013.01)

(58) Field of Classification Search
None
See application file for complete search history.

(56) References Cited

U.S. PATENT DOCUMENTS 7,655,752 B2    2/2010   Levine et al.

FOREIGN PATENT DOCUMENTS

| WO | WO 2005/030798 | 4/2005 |
| WO | WO 2013/168164 | 11/2013 |

OTHER PUBLICATIONS

Kirkegaard et al., Clin. Exp. Immunol., vol. 135, pp. 146-153, 2004.*
International Preliminary Report on Patentability Dated Nov. 20, 2014 From the International Searching Authority Re. Application No. PCT/IL2013/050400.
International Search Report and the Written Opinion Dated Oct. 11, 2013 From the International Searching Authority Re. Application No. PCT/IL2013/050400.
Buckley et al "Amino-Terminal TACE Prodomain Attenuates TNFR2 Cleavage Independently of the Cysteine Switch", American Journal of Physiology, Lung Cellular and Molecular Physiology, 288(6): L1132-L1138, Jun. 2005.
Gonzales et al. "Inhibition of the Tumor Necrosis Factor-Alpha-Converting Enzyme by Its Pro Domain", The Journal of Biological Chemistry, XP002713545, 279(30): 31638-31645, Jul. 23, 2004.
Hoth et al. "Expression and Protein Chemistry Yielding Crystallization of the Catalytic Domain of ADAM17 Complexed With a Hydroxamate Inhibitor", Protein Expression and Purification, 52: 313-319, 2007.
Leonard et al. "Chaperone-Like Properties of the Prodomain of TNF[Alpha]-Converting Enzyme (TACE) and the Functional Role of Its Cysteine Switch", Biochemistry Journal, 387(Pt.3): 797-805, 2005.
Li et al. "The Study of the Inhibition of the Recombinant TACE Prodomain to Endotoxemia in Mice", International Journal of Molecular Sciences, XP009172684, 10(12): 5442-5454, Dec. 18, 2009.
Maskos et al. "Crystal Ctructure of the Catalytic Domain of Human Tumor Necrosis Factor-Alpha-Converting Enzyme", Proc. Natl. Acad. Sci. USA, 95(7): 3408-3412, Mar. 1998.
Wong et al. "The Tumor Necrosis Factor-A Converting Enzyme (TACE) is Regualted by Physiological Ionic Strength", Advances in Experimental Medicine and Biology, XP009172659, 691: #796, Appendix II, Jan. 1, 2011.
Office Action Dated Jan. 18, 2016 From the Israel Patent Office Re. Application No. 235592 and Its Translation Into English.

* cited by examiner

*Primary Examiner* — Richard Hutson

(57) ABSTRACT

A method of treating an inflammatory disease is disclosed. The method comprises administering to the subject a therapeutically effective amount of a polypeptide comprising a pro-domain of TNF-alpha converting enzyme (TACE), said polypeptide being devoid of a catalytic domain of said TACE, said polypeptide comprising a modification at a site selected from the group consisting of $R^{58}$, $R^{56}$ and $K^{57}$ which renders said polypeptide resistant to furin degradation said polypeptide being capable of downregulating an activity of TACE, thereby treating the inflammatory disease.

6 Claims, 14 Drawing Sheets
(10 of 14 Drawing Sheet(s) Filed in Color)

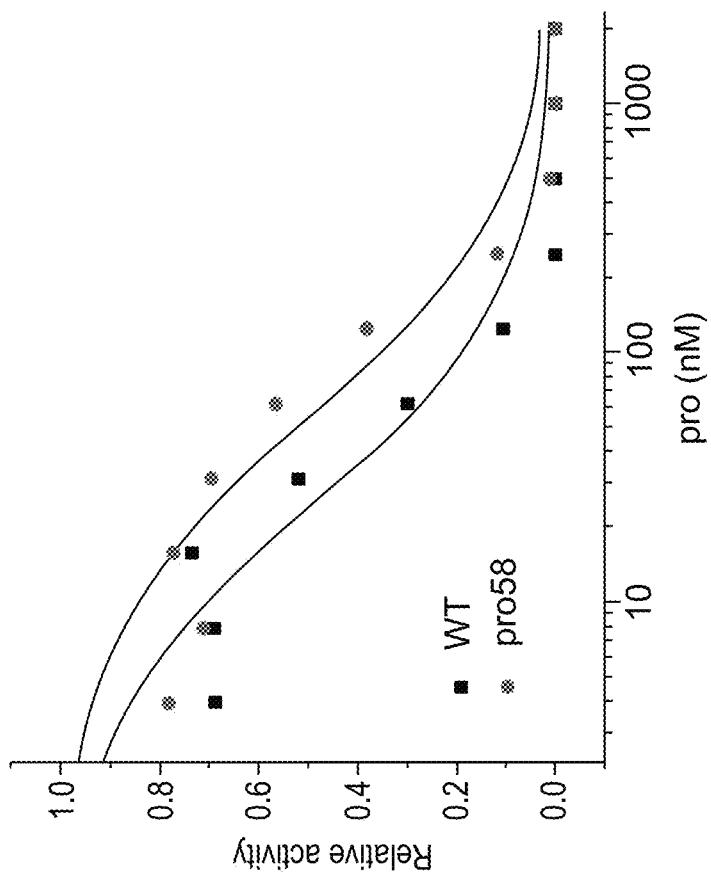
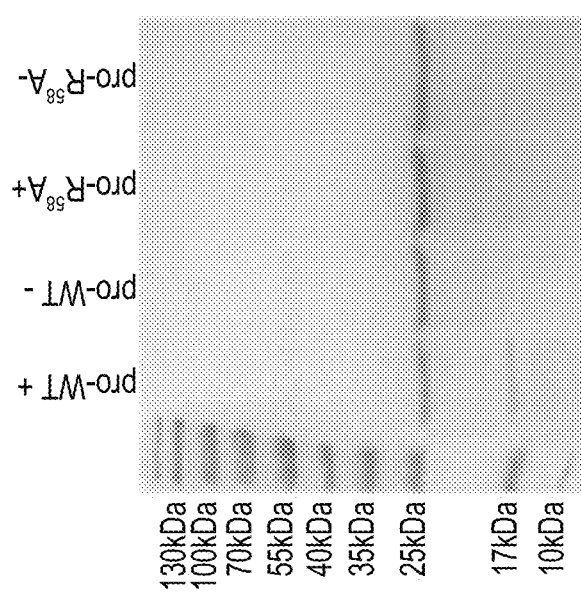
FIG. 10B
FIG. 10A

VARIANTS OF TACE PRO-DOMAIN AS TNF-A INHIBITOR AND THEIR MEDICAL USE

RELATED APPLICATIONS

This application is a National Phase of PCT Patent Application No. PCT/IL2013/050400 having International filing date of May 9, 2013, which claims the benefit of priority under 35 USC §119(e) of U.S. Provisional Patent Application No. 61/644,551 filed on May 9, 2012. The contents of the above applications are all incorporated by reference as if fully set forth herein in their entirety.

SEQUENCE LISTING STATEMENT

The ASCII file, entitled 60524SequenceListing.txt, created on Sep. 21, 2014 comprising 27,753 bytes, submitted concurrently with the filing of this application is incorporated herein by reference.

FIELD AND BACKGROUND OF THE INVENTION

The present invention, in some embodiments thereof, relates to TNF alpha convertase inhibitors (TACE inhibitors) for the treatment of inflammatory disorders including Crohn's disease and rheumatoid arthritis.

Members of the ADAM family have been recognized as major ectodomain shedding proteinases. ADAMs are mostly type I transmembrane proteins featuring a multi-domain structure consist of pro-domain, a catalytic domain, a disintegrin domain, an EGF-like (cysteine-rich) domain, a single transmembrane domain and a cytoplasmic portion (FIG. 1). The pro-domain inhibits ADAM proteinase activity by binding the catalytic Zn(II) while mediating specific protein-protein interactions with the enzyme active site surface. This domain is cleaved by another proteinase either intra or extra cellular to regain enzyme activity. ADAM disintegrin-domains can, in some cases, interact with integrins to influence cell adhesion and cell-cell interactions. The disintegrin- and/or EGF-like-domains are thought to be involved in substrate recognition and/or (hetero)-dimerization. The transmembrane region is followed by a C-terminus cytoplasmic region, which contains an SH3-binding motif that interacts with intracellular signaling proteins.

Up to date most of the examined shedding activity on the cell surface is mediated by ADAM17 and its close relative ADAM10. A large number of proteins were identified as substrates for ADAM17 including key immuno-regulatory cytokines like TNF-α, IL-6 and their receptors TNFR and IL-6R, cancer related molecule such as ErbB ligands and their receptors, signaling molecule as Notch-1, cell adhesion molecules such as L-selectin (CD62L) or ICAM-1 and even amyloid precursor protein. Since ADAM17 had been identified as the primary sheddase for TNF-α it was named the TNF-α converting enzyme—TACE. Hence large variable biological functions are linked to ADAM17, such as development, axon guidance, cell-cell interactions, signaling and its main role in releasing TNF-α in inflammation.

Despite the remarkably large number of ADAM17 substrates identified during the last decade, most of the proposed pathological roles of this metalloproteinase are related to just a few substrates including pro-TNF-α, the ligands of the EGFR and the Amyloid Precursor Protein (APP) (FIG. 2). Given the central role of these molecules in many biological processes, the number of diseases in which ADAM17 has been suggested as a therapeutic target has grown exponentially in the last years. Many compounds belonging to different chemical classes have been synthesized as selective TACE inhibitors. However, the tested small molecules have been withdrawn from Phase II clinical trials for rheumatoid arthritis because of lack of efficacy, specificity and hepatotoxicity in vivo [DasGupta, S., et al., Bioorg Med Chem, 2009. 17(2): p. 444-59]. This result is not surprising. The use of synthetic small molecule inhibitors suffers from a lack of specificity. The small molecule inhibitors targeted the active site of TACE, which is highly conserved among all members of the metazincin family (FIG. 3). Therefore, many unpredicted side-effects were encountered by unwanted cross inhibition [Moss, M. L., et al Nat Clin Pract Rheumatol, 2008. 4(6): p. 300-9].

Inhibition in vivo is achieved by the naturally occurring endogenous MMP inhibitors, the Tissue Inhibitors of Metalloproteinases family (TIMP). This family consists of 4 members, namely TIMP1-4, which exhibit high sequence homology. Under normal physiological conditions, the activity of MMPs is mostly regulated by the TIMPs. Misregulation can lead to arthritis, cancer, multiple sclerosis and cardiovascular disease. Interestingly, the N-terminal domains can fold independently and fully inhibit the activity of the targeted MMPs or ADAMs. The inhibition mechanism involves a direct coordination of the catalytic Zn(II) via an N-terminal cysteine of the TIMPs as well as protein-protein interactions with the enzyme extended catalytic cleft. This confirms the mechanistic importance of metal chelation by the N-terminal amino group in metalloproteinase inhibitory activity. The selectivity towards a targeted MMP is achieved by four residues in the N-terminus populating the catalytic cleft by backbone contacts mimicking a binding of a substrate. Interestingly, an overall topology view reveals a "lock and key" protein-protein interactions that take place between the surface residues of the MMPs and the TIMPs (FIGS. 4A-B). TACE is naturally inhibited by TIMP-3 as shown in the crystal structure by Wisniewska et al 2008 [J Mol Biol, 2008. 381(5): p. 1307-19].

Similar to other members of the MMP family, TACE is generated as a latent zymogen and is activated upon the release of the inhibitory pro-domain. The activation of TACE zymogen is performed mainly by Furin-like protease, a proprotein convertase, in the late Golgi compartment through a Furin consensus site in the junction between pro-domain and the catalytic-domain $^{211}RVKR^{214}/R^{215}$. It has been found that the TACE pro-domain is essential for secretion of this enzyme in a functional form. TACE expression constructs that lack the pro-domain failed to secrete as a functional enzyme in insect cells and the protein retained in the endoplasmic reticulum and subject to degradation. It was concluded that the TACE pro-domain work as an intramolecular chaperone, assisting in the secretion of this proteinase.

The cytokine TNF-α plays a major role in autoimmune disease processes in inflammatory bowel disease and rheumatoid arthritis. Therefore, TNF-α has become an important target for the development of therapeutic strategies for the treatment of Crohn's disease and rheumatoid arthritis. TNF-α inhibitors that have been approved for clinical use to treat autoimmune disorders are infliximab, adalimumab and etanercept. Infliximab and adalimumab are modified antibodies specific for TNF-α whereas, Etanercept is a fusion protein comprising the ligand-binding portion of the human p75 TNF receptor (TNFRII) and the Fc fragment of human IgG1. The TNF-α inhibitors block the interaction of TNF-α with cell-surface receptors (FIG. 5).

A different strategy, highlighted by the design of small molecule inhibitors, is to prevent the release of soluble TNF-α from its membrane bound precursor. TACE being the major sheddase for TNF-α in immune-competent cells became a rationale target for this strategy. Orally available small molecule inhibitors were developed and demonstrate improved selectivity for TACE over the closely related matrix metalloproteinases [Georgiadis, D. and A. Yiotakis, Bioorg Med Chem, 2008. 16(19): p. 8781-94]. However, all of them failed due to liver toxicity caused by the unspecific side-effects of cross inhibition of other members of the MMP family.

Use of the pro-domain to inhibit TACE has been disclosed in Leonard, J. D., et al. Biochem J, 2005. 387(Pt 3): p. 797-805; Gonzales, P. E., et al., J Biol Chem, 2004. 279(30): p. 31638-45; Maskos, K., et al. Proc Natl Acad Sci USA, 1998. 95(7): p. 3408-12; Li et al., Int J Mol Sci. 2009 December; 10(12): 5442-5454; Buckley Am J Physiol Lung Cell Mol Physiol 288: L1132-L1138, 2005. U.S. Pat. No. 7,655,752 teaches TACE pro-domain and fragments thereof for the treatment of cancer and other diseases.

SUMMARY OF THE INVENTION

According to an aspect of some embodiments of the present invention there is provided a method of treating an inflammatory disease, the method comprising administering to the subject a therapeutically effective amount of a polypeptide comprising a pro-domain of TNF-α converting enzyme (TACE), the polypeptide being devoid of a catalytic domain of the TACE, the polypeptide comprising a modification at a site selected from the group consisting of $R^{58}$, $R^{56}$ and $K^{57}$ which renders the polypeptide resistant to furin degradation the polypeptide being capable of downregulating an activity of TACE, thereby treating the inflammatory disease.

According to an aspect of some embodiments of the present invention there is provided an isolated polypeptide comprising a pro-domain of TNF-α converting enzyme (TACE), the polypeptide being devoid of a catalytic domain of the TACE, the polypeptide comprising a modification at a site selected from the group consisting of $R^{58}$, $R^{56}$ and $K^{57}$ which renders the polypeptide resistant to furin degradation the polypeptide being capable of downregulating an activity of TACE.

According to an aspect of some embodiments of the present invention there is provided method of generating a TACE pro-domain comprising expressing the isolated polypeptide described herein in a cell thereby generating the TACE pro-domain.

According to an aspect of some embodiments of the present invention there is provided a pharmaceutical composition comprising as an active component a polypeptide and a pharmaceutically active carrier, the polypeptide comprising a pro-domain of TNF-α converting enzyme (TACE), the polypeptide being devoid of a catalytic domain of the TACE, the polypeptide comprising a modification at a site selected from the group consisting of $R^{58}$, $R^{56}$ and $K^{57}$ which renders the polypeptide resistant to furin degradation the polypeptide being capable of downregulating an activity of TACE.

According to an aspect of some embodiments of the present invention there is provided an isolated polynucleotide encoding the polypeptide described herein.

According to an aspect of some embodiments of the present invention there is provided a bacterial cell comprising a TACE pro-domain in the cytosol and not in an inclusion body.

According to an aspect of some embodiments of the present invention there is provided a method of generating a TACE pro-domain comprising a modification at a position C184, the method comprising expressing the TACE pro-domain in a cytoplasm of a bacterial cell, thereby generating the TACE pro-domain.

According to some embodiments of the invention, the modification is at $R^{58}$.

According to some embodiments of the invention, the isolated polypeptide is for use in treating an inflammatory disease.

According to some embodiments of the invention, the isolated polypeptide is soluble when expressed in bacterial cells.

According to some embodiments of the invention, the isolated polypeptide is expressed in the cytosol of the bacterial cells and not in inclusion bodies.

According to some embodiments of the invention, the inflammatory disease is an autoimmune disease.

According to some embodiments of the invention, the autoimmune disease is Crohn's disease or rheumatoid arthritis.

According to some embodiments of the invention, the inflammatory disease is cancer.

According to some embodiments of the invention, the inflammatory disease is hepatitis.

According to some embodiments of the invention, the inflammatory disease is associated with an immune response associated with cell, tissue or organ transplantation.

According to some embodiments of the invention, the TACE pro-domain comprises an amino acid sequence at least 90% homologous to the sequence as set forth in SEQ ID NO: 5 as determined by BlastP using default parameters.

According to some embodiments of the invention, the polypeptide further comprises a modification at a position selected from the group consisting of $R^{211}$, $R^{214}$ and $C^{184}$.

According to some embodiments of the invention, the modification at position 58 is a replacement of arginine to alanine.

According to some embodiments of the invention, the modification at position 211 is a replacement of arginine to alanine.

According to some embodiments of the invention, the modification at position 214 is a replacement of arginine to glycine.

According to some embodiments of the invention, the modification at position 184 is a replacement of cysteine to alanine.

According to some embodiments of the invention, the pro-domain of TACE comprises a sequence selected from the group consisting of SEQ ID NOs. 6-8.

According to some embodiments of the invention, the polypeptide further comprises a modification at position a position selected from the group consisting of $R^{211}$, $R^{214}$ and $C^{184}$.

According to some embodiments of the invention, the polypeptide is a recombinant polypeptide.

According to some embodiments of the invention, the recombinant polypeptide is generated in bacteria.

According to some embodiments of the invention, the pro-domain of TACE is attached to a heterologous polypeptide.

According to some embodiments of the invention, the heterologous polypeptide is selected from the group consisting of human serum albumin, immunoglobulin, and transferrin.

According to some embodiments of the invention, the immunoglobulin comprises an Fc domain.

According to some embodiments of the invention, the pro-domain of TACE is attached to a polymer.

According to some embodiments of the invention, the polymer is selected from the group consisting of a polycationic polymer, a non-ionic water-soluble polymer, a polyether polymer and a biocompatible polymer.

According to some embodiments of the invention, the polymer is poly(ethylene glycol).

According to some embodiments of the invention, the isolated polynucleotide has a codon usage optimized for expression in bacteria.

According to some embodiments of the invention, the isolated polynucleotide comprises a nucleic acid sequence selected from the group consisting of SEQ ID NOs. 11-16.

According to some embodiments of the invention, the TACE pro-domain is soluble.

According to some embodiments of the invention, the amino acid sequence of the TACE pro-domain is set forth in SEQ ID NOs: 5, 6, 7 or 8.

According to some embodiments of the invention, the soluble TACE pro-domain is encoded by a nucleic acid sequence comprising a sequence selected from the group consisting of SEQ ID NOs: 11-16.

According to some embodiments of the invention, the cell is a bacterial cell.

According to some embodiments of the invention, the bacterial cell is an *E. coli* cell.

According to some embodiments of the invention, the expressing is effected by introducing a nucleic acid construct comprising a nucleic acid sequence which encodes the polypeptide into the cell.

According to some embodiments of the invention, the nucleic acid sequence is selected from the group consisting of SEQ ID NOs: 11-16.

According to some embodiments of the invention, the pro-domain is not expressed in an inclusion body.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
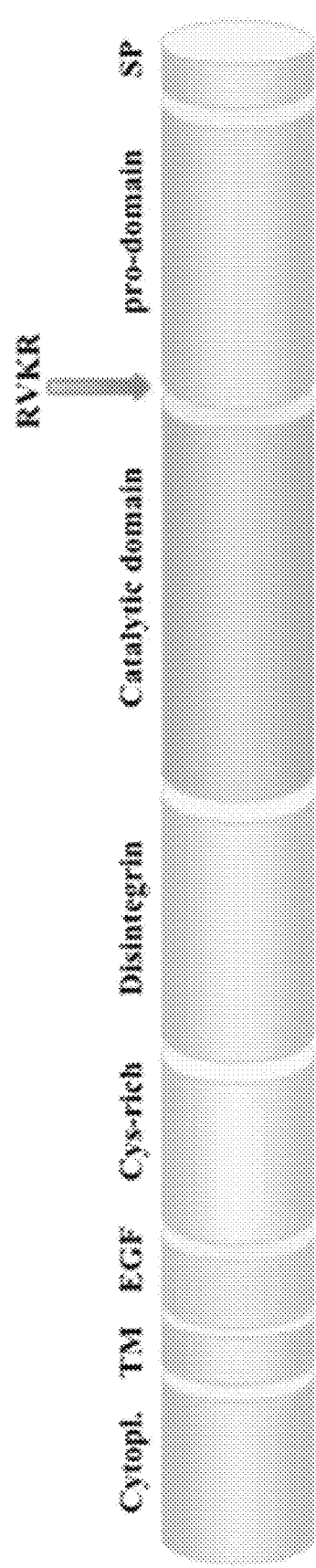

FIG. 1 is a schematic presentation of TACE domains. SP— signal peptide responsible for directing TACE to the membrane. TACE pro-domain-serves inactivation of catalytic activity and chaperone. Arrow indicating the cleavage site of Furin for zymogen maturation. Catalytic domain-cleavage substrates. Disintegrin-interaction with integrin. Cys-rich-maturation. Cytopl.-interaction with signal molecules.

Figure 2:
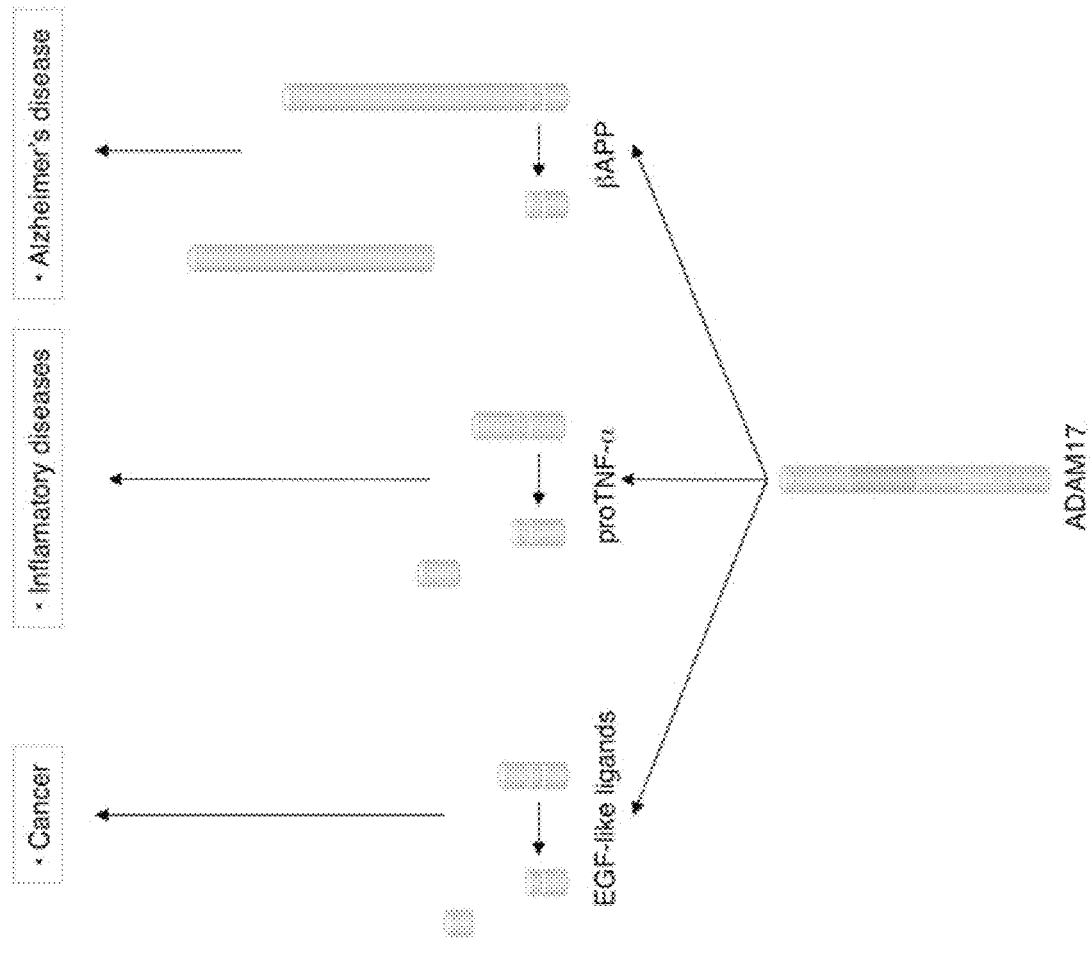

FIG. 2 is a schematic showing the types of diseases in which ADAM17 is involved, through the cleavage of EGF like ligands, proTNF-alpha and betaAPP.

Figure 3:
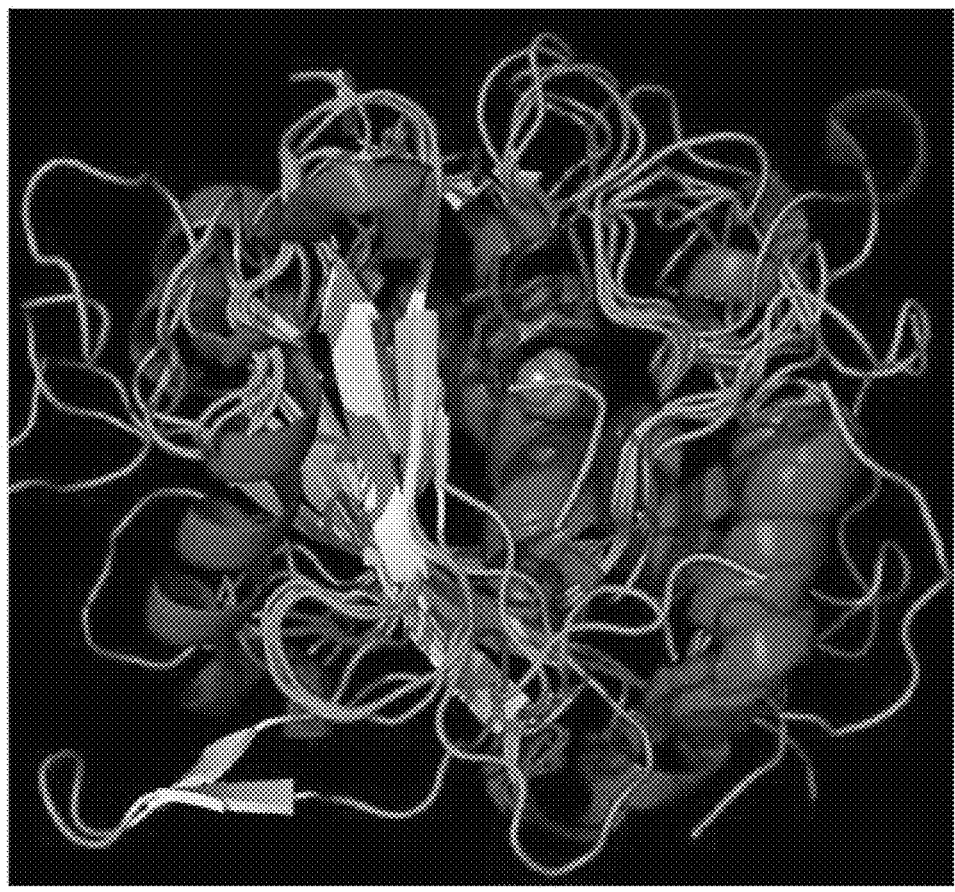

FIG. 3 is a structure alignment of MMP1, MMP7, MMP9, MT1 and TACE catalytic domains. Grey spares represent the catalytic Zn(II) in each structure, Blue-small molecule inhibitor.

Figure 4A:
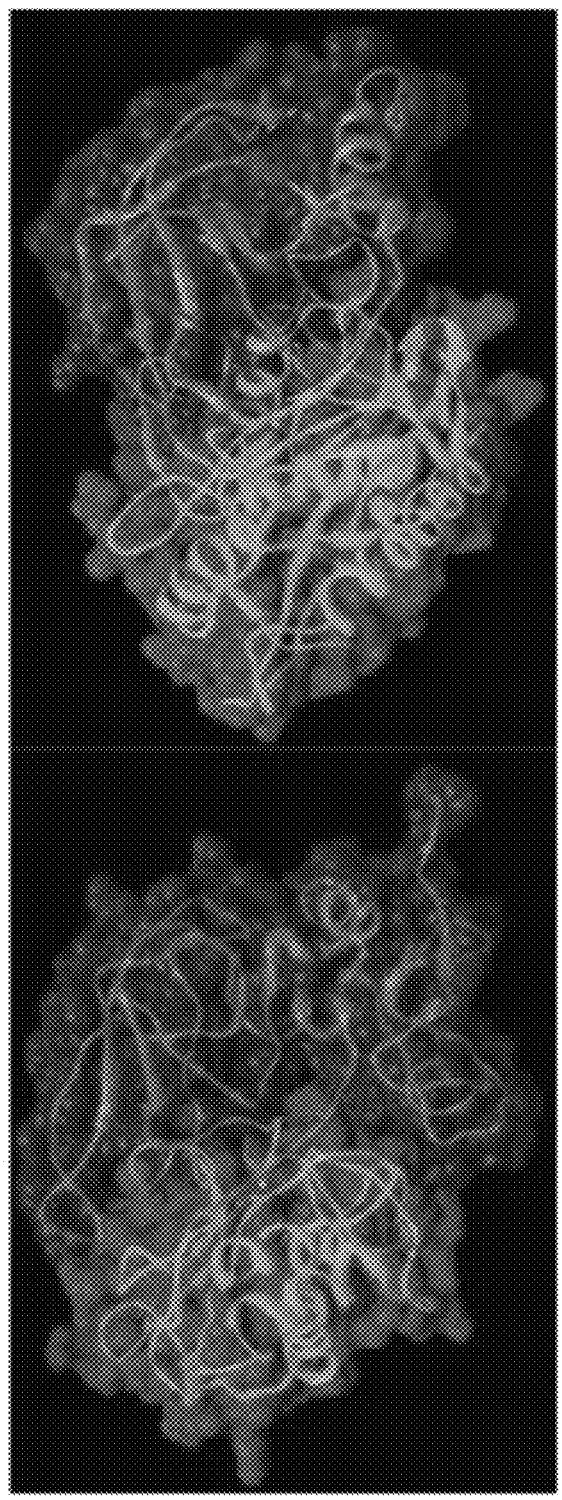
Figure 4B:
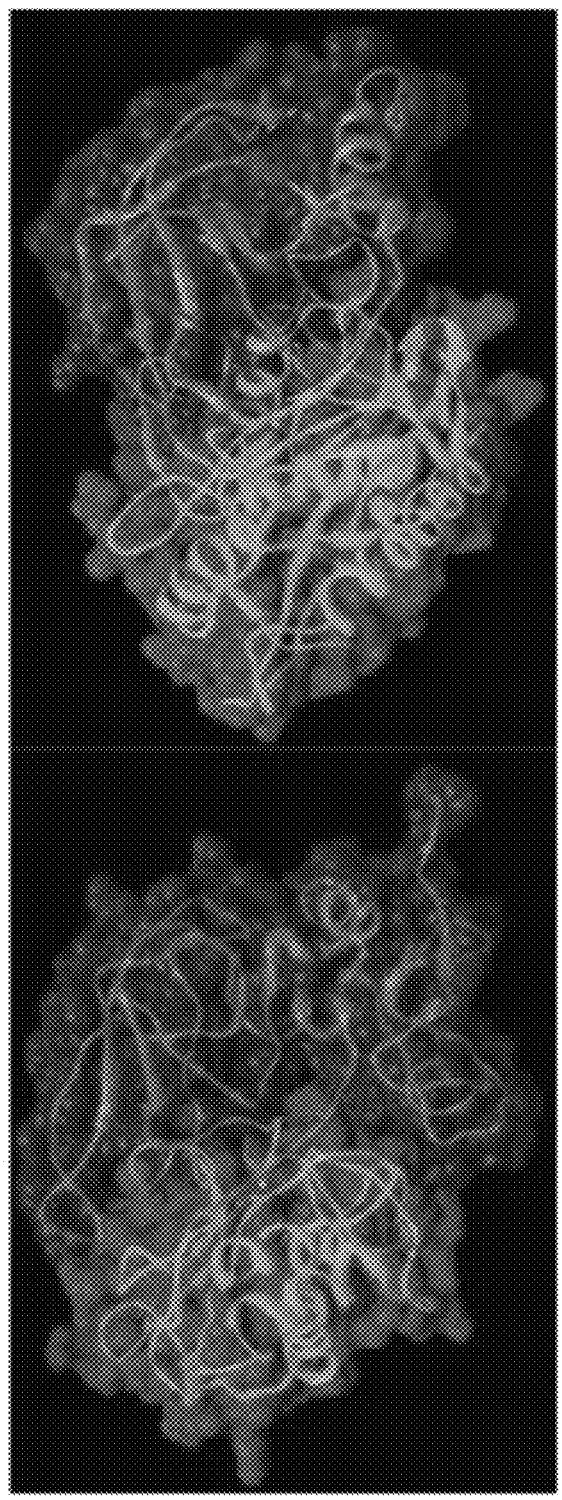

FIGS. 4A-B illustrate TIMP inhibition on TACE and MT1. FIG. 4A (PDB file 1BBQ), MT1 (green) inhibited by TIMP-2 (red) grey sphere represents the catalytic Zn(II). FIG. 4B (PDB file 3CKI), TACE (green) inhibited by TIMP-3 (red) grey sphere represents the catalytic Zn(II), which held by 3 coordination interactions with 3 histidine residues and a cysteine residue contributed by the related TIMP.

Figure 5:
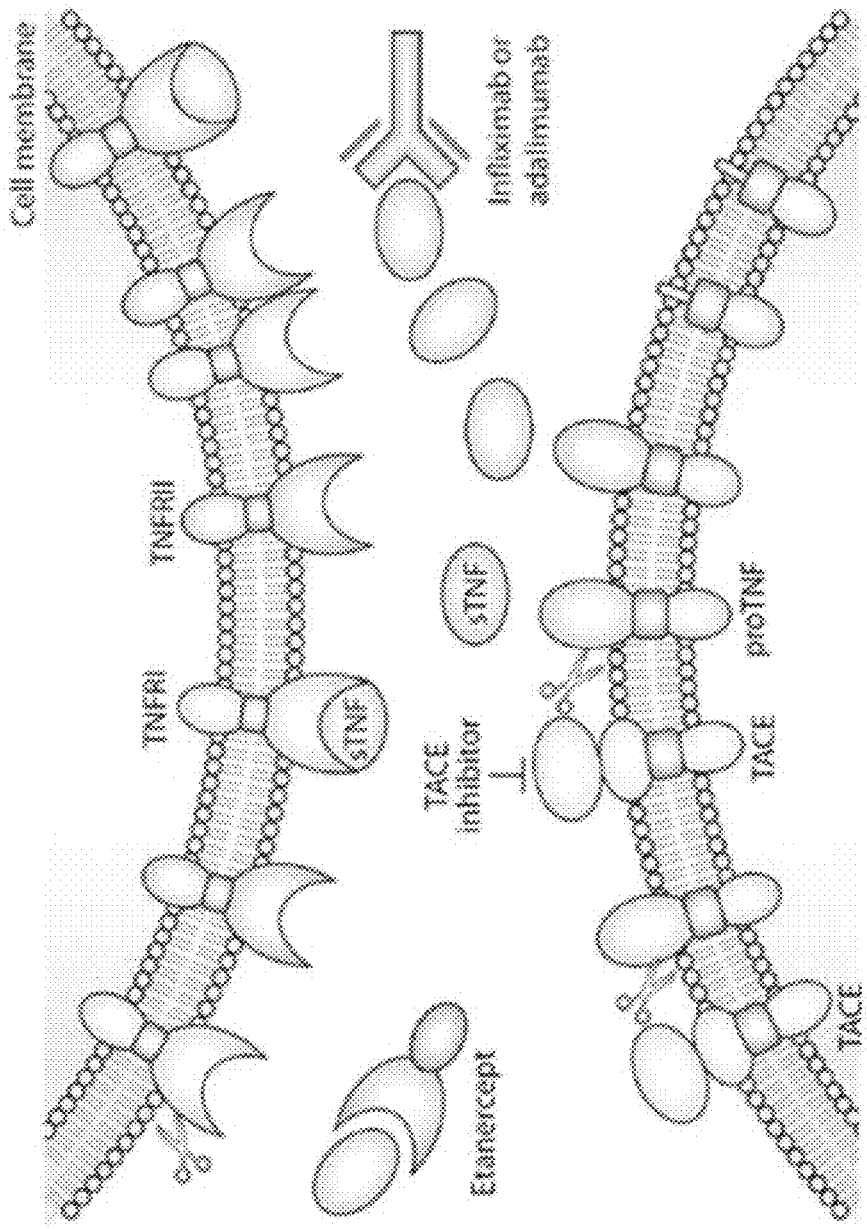

FIG. 5 illustrates anti-TNF therapies and their effect on TNF-α. Etanercept, a fusion protein of TNFRII and the Fc region of IgG1, and the anti-TNF antibodies infliximab and adalimumab, bind to TNF-α and prevent the molecule from binding to the receptor.

Figure 6A:
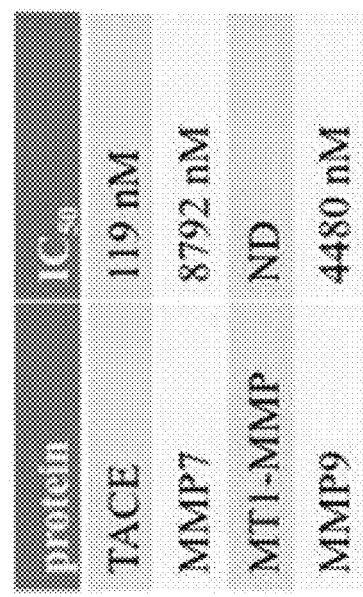
Figure 6B:
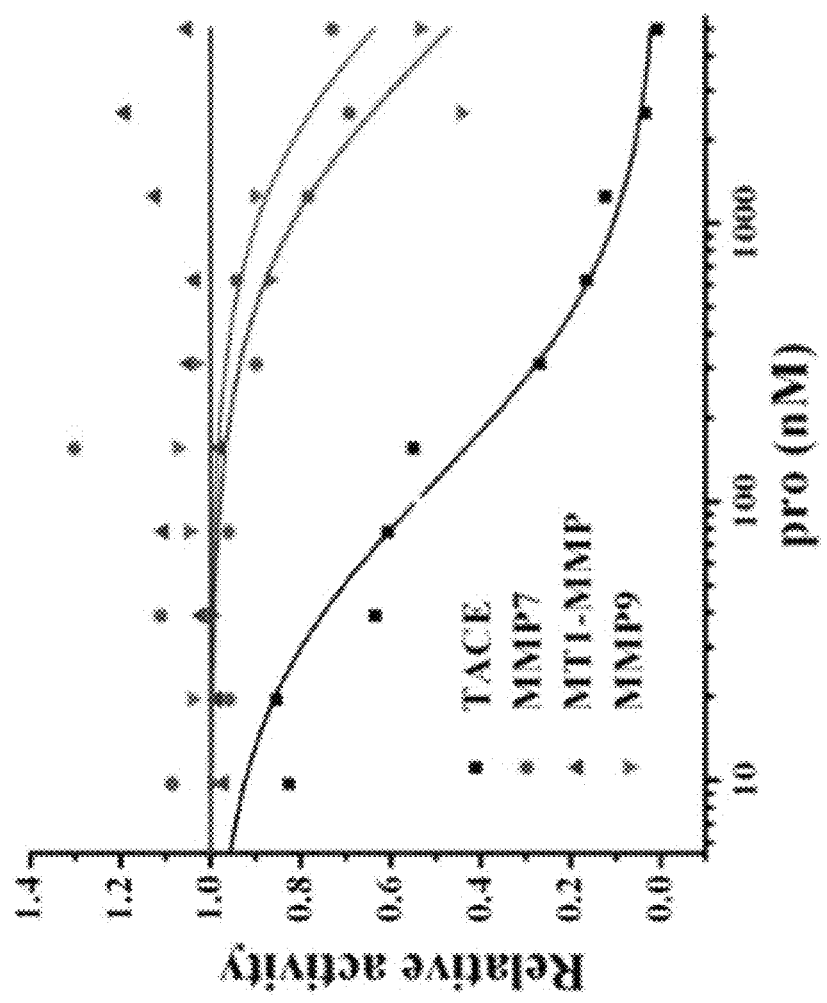

FIGS. 6A-B illustrate in vitro selective inhibition of TACE pro-domain. (A) Catalytic activity of TACE (black square), MMP7 (red circle), MT1-MMP (blue triangle) and MMP9 (green triangle) on flourogenic peptide in presents of TACE pro-domain. (B) Calculated $IC_{50}$ values of TACE (119 nM), MMP7 (8792 nM), MT1-MMP (not determined) and MMP9 (4480 nM).

Figure 7B:
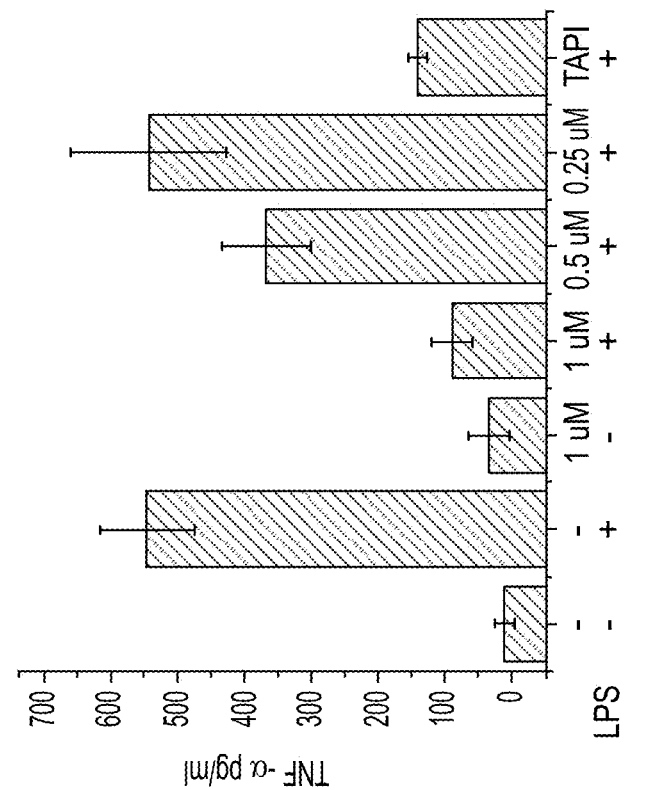
Figure 7A:
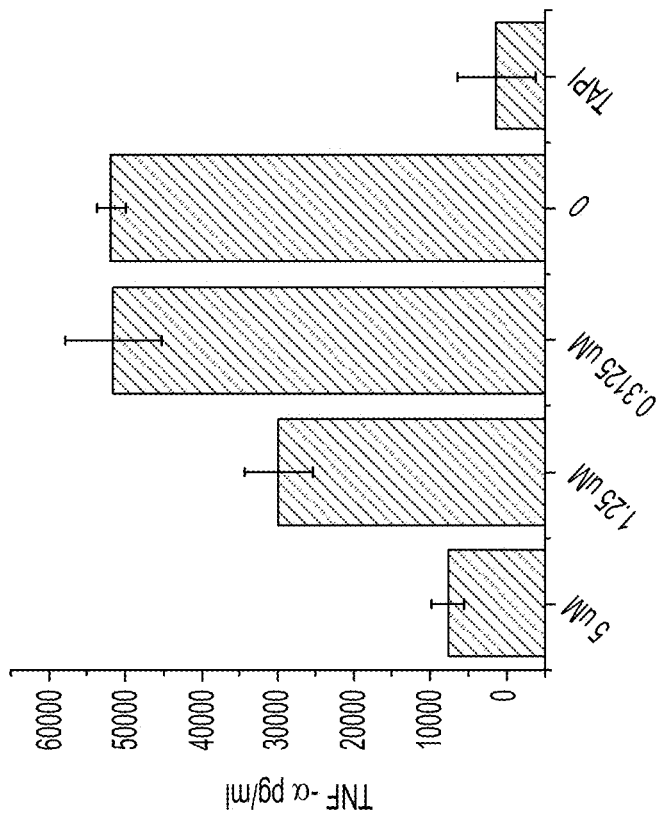

FIGS. 7A-B are graphs illustrating that the TACE pro-domain inhibits TNF-α secretion in cell-based assay. Secretion of TNF-α in CHO transfected TNF-α cells (A) and primary macrophages (B). LPS (Lipopolysaccharide) is used to stimulate TACE presentation on cell surface. TAPI (small molecule inhibitor targeting TACE) is used as positive control in this assay.

FIGS. 8A-F illustrate that treatment with TACE pro-domain protects against TNBS colitis development. A-F Clinical colitis severity was monitored by weight loss (A), survival (B), macroscopic score (C), histopathologic analysis performed in hematoxylin/eosin-stained sections of colons (D), representative colons feature groups (E) and histologic features of representative colonic sections at ×10 magnification of TNBS induced control colon and colon of TNBS induced mice treated with TACE pro-domain (F).

Figures 9A, 9B:
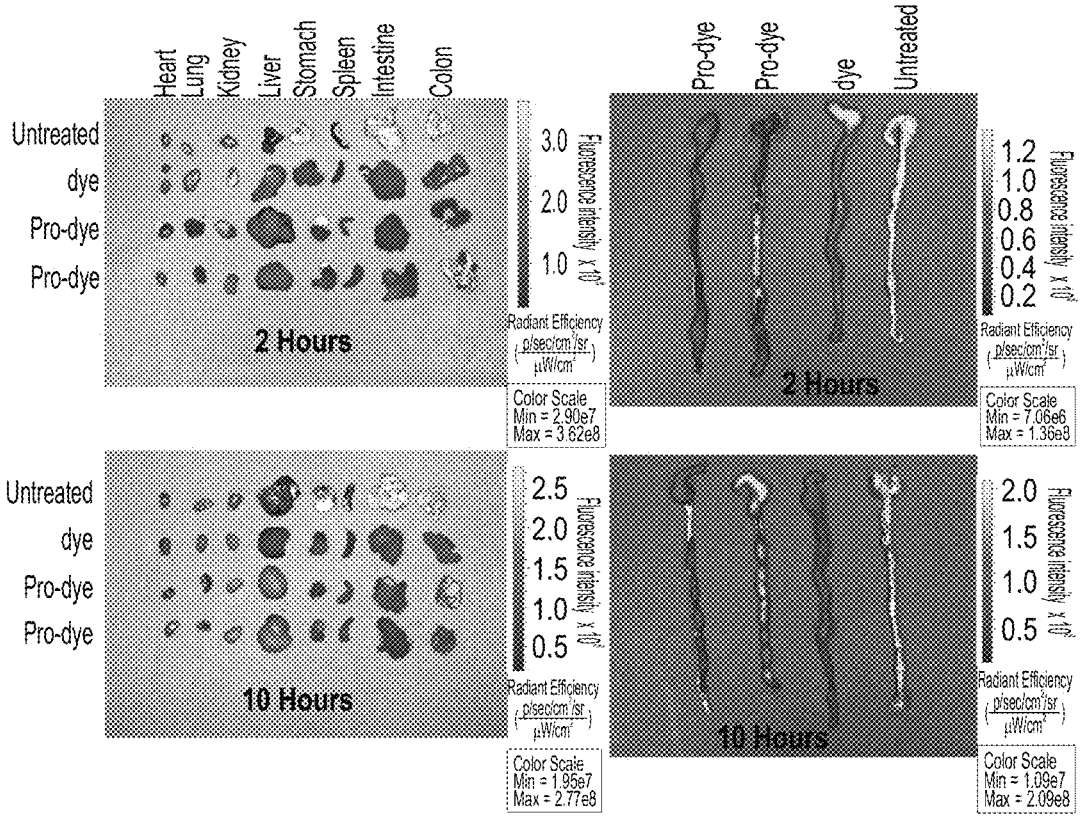
Figure 9C:
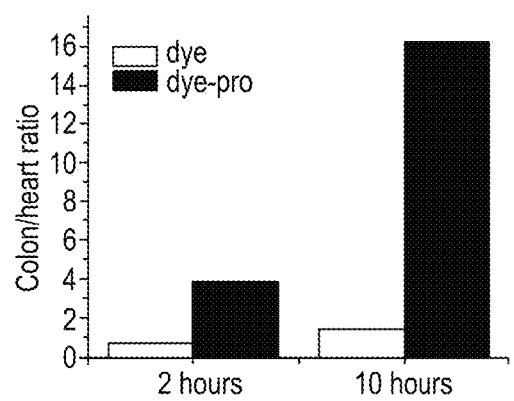

FIGS. 9A-C illustrate fluorescence imaging analysis on fresh tissues using labeled TACE pro-domain. Representative images of dissected organs (A) or spread colons (B) of TNBS treated or healthy mice sacrificed 2 h or 10 h following intravenous injection fluorescently labeled TACE pro-domain (1.5 nmol of SDS3-HiLyte Fluor 750) or fluorescent dye only (1.5 nmol of Hilyte Fluor 750). (C) Colon-to-heart ratios of the fluorescence for the mice sacrificed 2 and 10 hours following injection.

FIGS. 10A-B illustrate pro-$R^{58}$A resistance to proteolysis by Furin. (A) Reaction of pro-WT and pro-R58A with Furin (+)/without Furin (−). (B) Proteolytic activity of TACE in presents of pro-WT (square) and pro-R$^{58}$A (circle). The calculated IC50 are: pro=23 nM and pro58=55 nM.

Figure 11B:
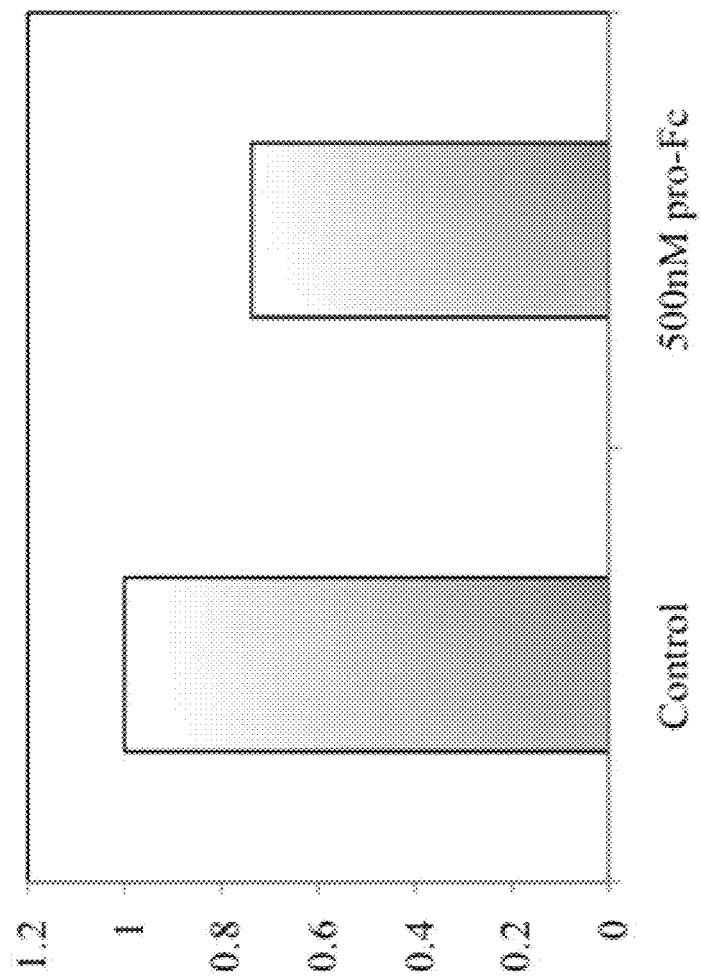
Figure 11A:
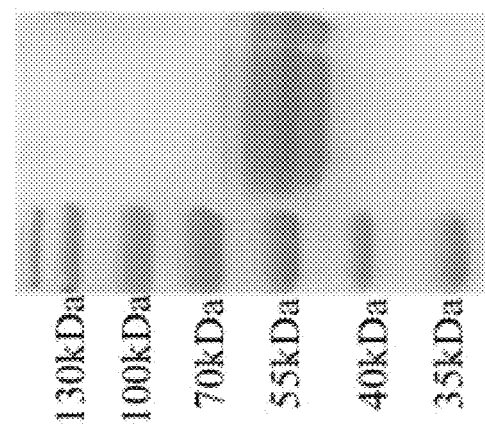

FIGS. 11A-B illustrate pro-Fc purification and inhibition. (A) SDS PAGE analysis of purified pro-Fc. (B) pro-Fc inhibits catalytic TACE activity in 25%.

Figure 12:
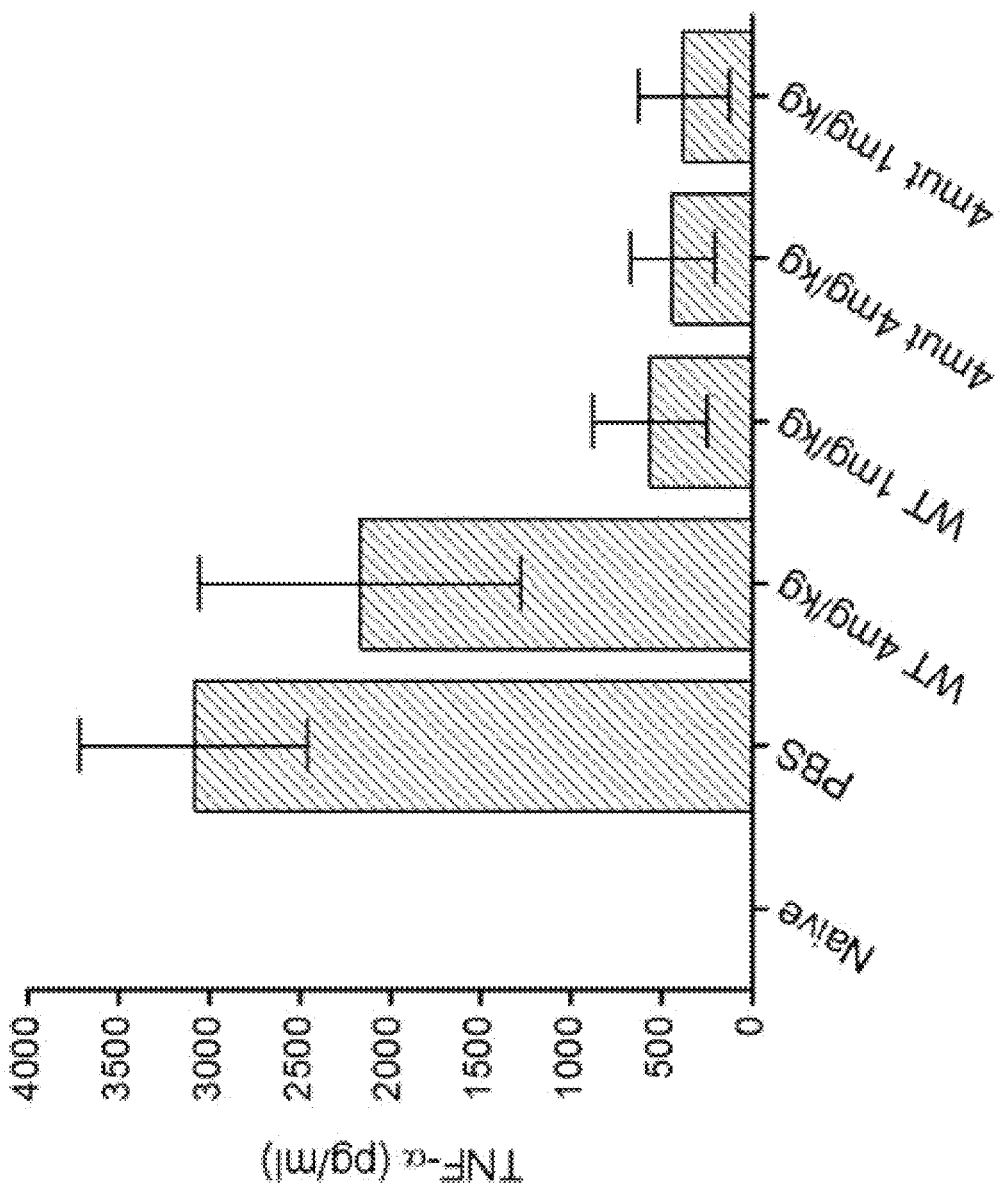

FIG. 12 illustrates WT TACE pro-domain and 4mut TACE pro-domain reduces serum TNF-α levels in LPS induced septic shock model. Serum level of TNF-α in naive C57/BL mice and C57/BL mice injected with control PBS and different concentration of TACE pro-domain 1 hour prior to 100 μg LPS injection. Blood was collected 1.5 hour following injection and the serum were test with standard TNF-α ELISA kit.

Figure 13C:
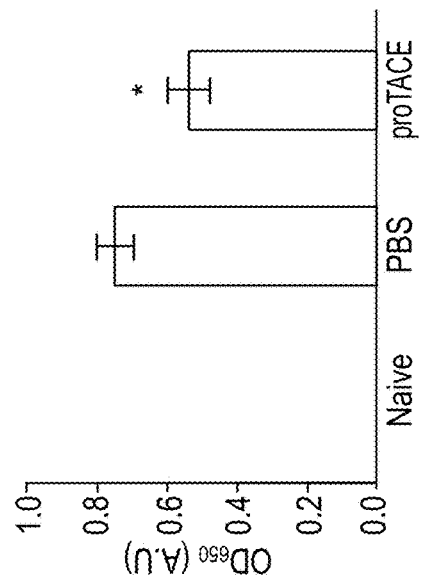
Figure 13B:
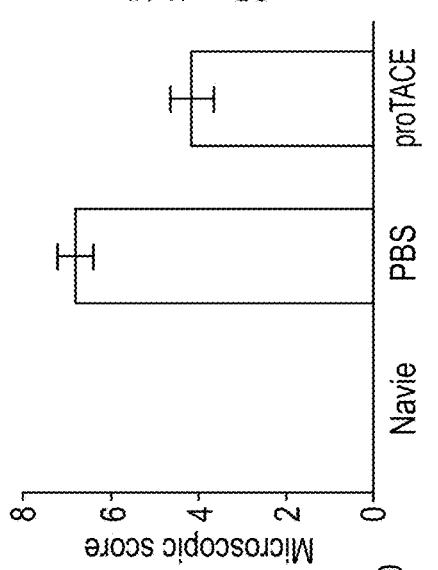
Figure 13A:
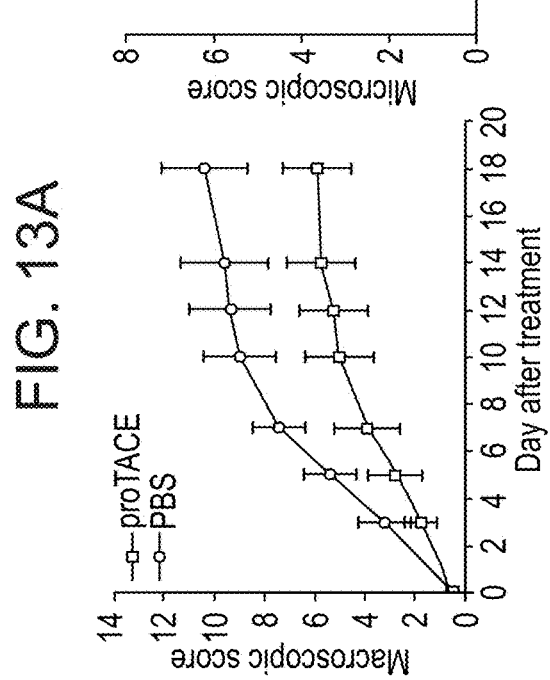

FIGS. 13A-C illustrate that treatment with TACE pro-domain protects against collagen induced arthritis (CIA). Arthritis was induced in DBA/1 mice by immunization with type II collagen and intravenous injection of TACE pro-domain 1 day after type II collagen boost and stopped after 10 days of daily injection. Macroscopic clinical score (A), histopathologic analysis performed in hematoxylin/eosin-stained sections of joints (B) serum from naïve, PBS control arthritic mice and TACE pro-domain treated were analysed for anti-collagen antibodies (C).

Figure 14:
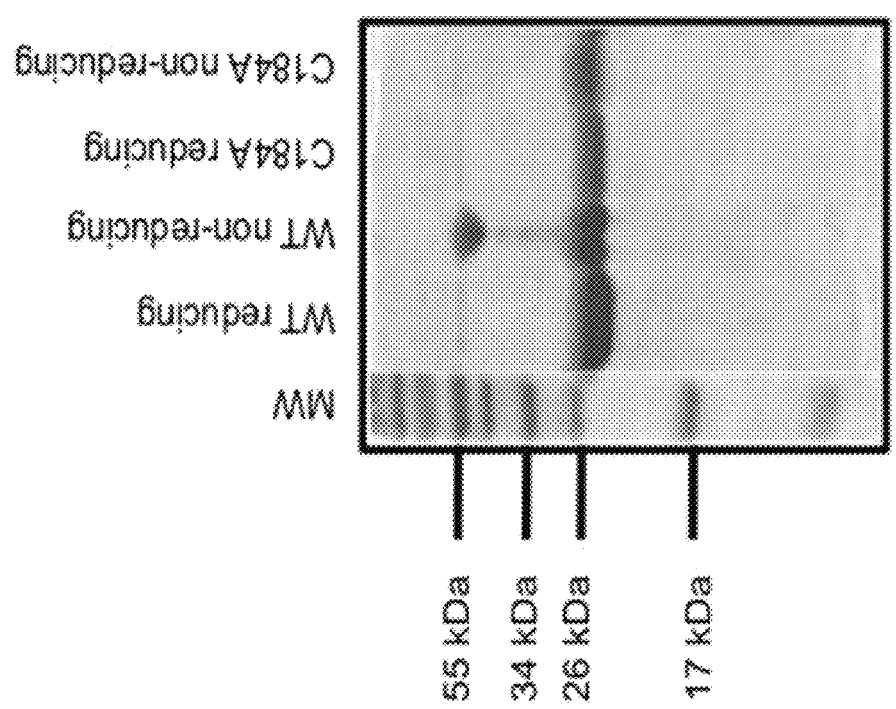

FIG. 14 is a photograph of an SDS Page gel illustrating that the C184A modification prevented dimerization under reducing and non-reducing conditions.

DESCRIPTION OF SPECIFIC EMBODIMENTS
OF THE INVENTION

The present invention, in some embodiments thereof, relates to TNF alpha convertase inhibitors (TACE inhibitors) for the treatment of inflammatory disorders including Crohn's disease and rheumatoid arthritis.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

TACE (tumor necrosis factor-α-converting enzyme; EC number 3.4.24.86), also called ADAM metallopeptidase domain 17 (ADAM17), is a 70-kDa enzyme that belongs to the ADAM protein family of disintegrins and metalloproteases.

Similar to other members of the Matrix metalloprotease (MMP) family, TACT is generated as a latent zymogen and is activated upon the release of the inhibitory pro-domain. The activation of TACE zymogen is performed mainly by a Furin-like protease, a proprotein convertase, in the late Golgi compartment through a Furin consensus site in the junction between pro-domain and the catalytic-domain $^{211}$RVKR$^{214}$/R$^{215}$ (SEQ ID NO: 20).

The present inventors have now uncovered a second non-canonical furin cleavage site —R$^{56}$KR$^{58}$/D$^{59}$ (SEQ ID NO: 22). This second cleavage site does not resemble the well-defined minimal Furin consensus site: Arg-X-X-Arg/X SEQ ID NO: 21) as defined by Molloy, S. S. et. al J. Biol. Chem. 1992, 267, 16396.

According to Nakayama, K. [Biochem J. 1997, 327(Pt 3), 625], other requirements for Furin recognition are:
(i) At the P1 position an Arg is essential;
(ii) In addition to the P1 Arg, at least two out of the three residues at P2, P4, and P6 are required to be basic for efficient cleavage;
(iii) At the P' 1 position, an amino acid with a hydrophobic side chain is not suitable.

The R$^{56}$KR$^{58}$/D$^{59}$ (SEQ ID NO: 22) site does not fit in with the basic requirements except for having an Arg at position P1. There are no Arg present at positions P2 (Lys), P4 (Val), and P6 (His) (HSVRKR/D) SEQ ID NO: 23).

The present inventors have shown that TACE pro-domain having a modification at position R$^{56}$ of the protein is more resistant to furin degradation than wild-type TACE pro-domain (FIGS. 10A-B).

Using a novel expression and purification system, the present inventors have succeeded in synthesizing large amounts of soluble TACE pro-domain in the bacterial cytosol. The pro-domain is present in its native folded state, thereby eliminating the need for subsequent complicated refolding steps.

Armed with a large supply of TACE pro-domain, the present inventors could now test this protein in relevant in vivo models for therapeutic activity.

Accordingly, the present inventors have demonstrated that administration of TACE pro-domain having a modification at position R$^{58}$ of the protein is more effective at preventing sepsis in an in vivo model as compared with the wild-type TACE pro-domain (FIG. 12).

Figure 8A:
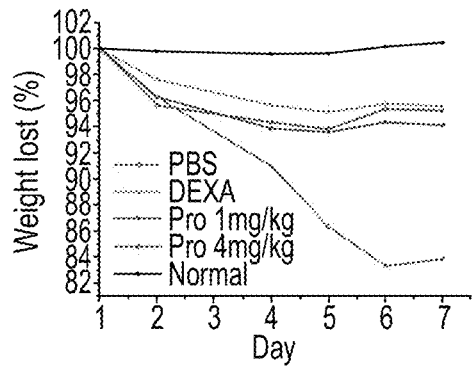
Figure 8B:
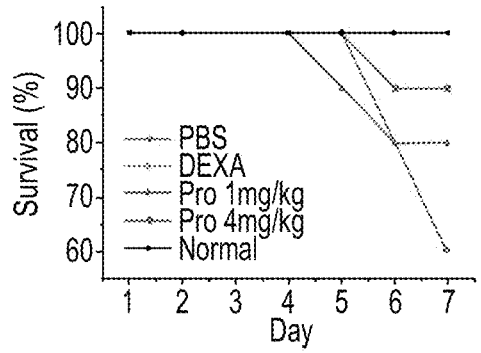
Figure 8C:
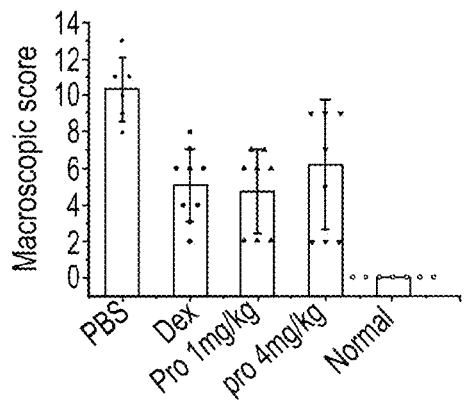
Figure 8D:
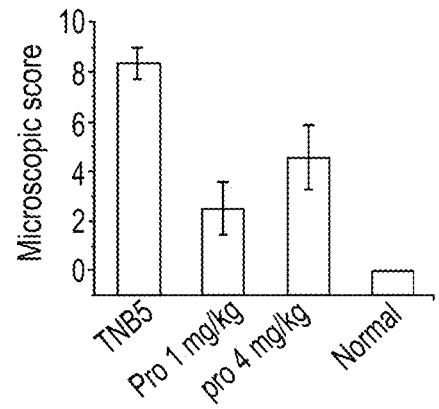
Figure 8E:
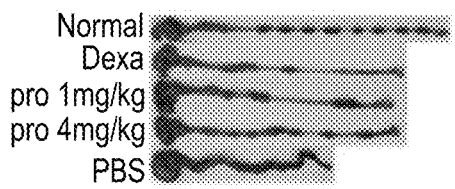
Figure 8F:
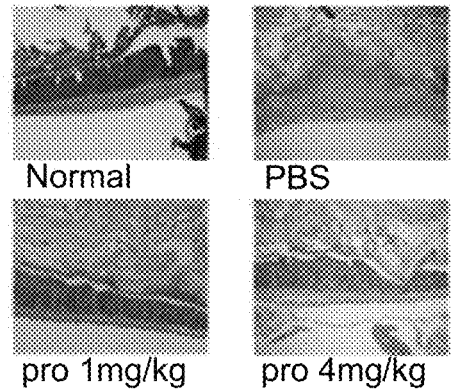

To evaluate the therapeutic potency of TACE pro-domain in autoimmune disease, an inflammatory bowel disease mouse model induced by TNBS/ethanol administration was used. Mice treated with the TACE pro-domain exhibited lower mortality and lower weight loss as compared to control mice (FIGS. 8A, B). The efficacy of the pro-domain was also apparent through an improvement in the macroscropic and histological scores (FIGS. 8C, D). The TACE pro-domain treated mice displayed a longer colon length, solid feces and fewer lesions (FIG. 8E). Moreover, the treatment also prevented massive infiltration of macrophages and immune cells to the colon lumen as seen in the PBS control (FIG. 8F).

FIGS. 9A-C demonstrates that TACE pro-domain could be detected from 10 hours after intravenous administration, in the colon of TNBS-treated mice located in focal patches along the colon (FIGS. 9A, B).

Overall, these results indicate that the inhibitory TACE pro-domain have a considerable efficacy in T helper cell-dependent inflammatory bowel disease states.

To evaluate the therapeutic potency of TACE pro-domain in an additional autoimmune disease, an arthritis mouse model induced by immunization of collagen type II was used.

As illustrated in FIGS. 13A-C, mice treated with TACE pro-domain displayed a significantly lower arthritis severity index (A), histological score (B), as well as lowered serum antibodies specific to type II collagen in a concentration-dependent manner (C) as compared to control.

Thus, according to one aspect of the present invention there is provided an isolated polypeptide comprising a pro-domain of TNF-α converting enzyme (TACE), the polypeptide being devoid of a catalytic domain of the TACE, the polypeptide comprising a modification at a site selected from the group consisting of R$^{58}$, R$^{56}$ and K$^{57}$ which renders the polypeptide resistant to furin degradation the polypeptide being capable of downregulating an activity of TACE.

As used herein, the phrase "pro-domain of TNF-α converting enzyme (TACE)" refers to the polypeptide portion of TACE that is responsible for maintaining the enzyme in its inactive form (i.e. not comprising catalytic activity).

According to one embodiment, the mutated pro-domain is derived from a human TACE, although other mammalian sequences of TACE are also contemplated.

The mRNA and amino acid sequences for *Homo sapiens* TACE can be found under GenBank accession number NM_003183.

According to a particular embodiment, the TACE pro-domain comprises the polypeptide sequence from $Asp^{23}$-$Arg^{214}$ of full length TACE.

As mentioned, the pro-domain of this aspect of the present invention is devoid of TACE catalytic (sheddase) activity.

As mentioned the TACE pro-domains described herein are capable of downregulating (e.g. inhibiting) an activity (e.g. sheddase activity or disintegrin activity) of TACE. By inhibit, it is intended to mean that the TACE activity is 5%, 10%, 15%, 20%, 25%, 30%, 35%, 40%, 45%, 50%, 55%, 60%, 65%, 70%, 75%, 80%, 85%, 90%, 95%, 96%, 97% or 98% less active relative to activity in the absence of the pro-domain. Methods of analyzing whether a TACE pro-domain polypeptide is capable of inhibiting TACE are described in the Examples section herein below.

The phrase "resistant to furin degradation" as used herein refers to having a higher resistance (at least 10% more resistant, at least 20% more resistant, at least 30% more resistant, at least 40% more resistant, at least 50% more resistant to furin degradation than the native sequence under the same reaction conditions. Analyzing the furin resistance of the polypeptide may be effected by incubating the polypeptide in the presence of furin and analyzing for the generation of fragments (e.g. by SDS gel analysis).

Contemplated modifications at the $R^{58}$, $R^{56}$ and $K^{57}$ position include a deletion or a replacement. It will be appreciated that the numbering of the mutations corresponds to the full length TACE enzyme and not the TACE pro-domain.

According to a particular embodiment, the $R^{58}$, $R^{56}$ and/or $K^{57}$ may be replaced by Alanine, Aspargine, Aspartic Acid, Cysteine, Glutamine, Glutamic Acid, Glycine, Histidine, Isolucine, Leucine, Methionine, Phenylalanine, Proline, Serine, Threonine, Tryptophan, Tyrosine or Valine.

According to another embodiment, the replacing amino acids are not positively charged amino acids—e.g. arginine or lysine.

Preferably, the Arginine at position 58 is replaced by Alanine—e.g. as set forth in SEQ ID NO: 6.

The present invention contemplates additional modifications (e.g. deletion of replacement) in the TACE pro-domain including, the canonical furin cleavage site including but not limited to a modification at any one of the positions including $R^{211}$, $R^{214}$. The present inventors further contemplate an amino acid modification at position $C^{184}$.

It will be appreciated that the present invention contemplates any combination of the modifications described herein above, for example, at least two, at least three or all four modifications described herein above (see for example SEQ ID NO: 8).

According to a particular embodiment, the $R^{211}$ and/or the $R^{214}$ may be replaced by Alanine, Aspargine, Aspartic Acid, Cysteine, Glutamine, Glutamic Acid, Glycine, Histidine, Isolucine, Leucine, Methionine, Phenylalanine, Proline, Serine, Threonine, Tryptophan, Tyrosine or Valine.

According to a particular embodiment, the $C^{184}$ may be replaced by Arginine, Aspargine, Aspartic Acid, Glycine, Glutamine, Glutamic Acid, Histidine, Isolucine, Leucine, Methionine, Phenylalanine, Proline, Serine, Threonine, Tryptophan, Tyrosine or Valine.

Preferably, the modification at position 211 is a replacement of arginine to alanine.

Preferably, the modification at position 214 is a replacement of arginine to glycine.

More preferably, the modification includes replacement of arginine to alanine at position 211 and replacement of arginine to glycine at position 214 (see for example SEQ ID NO: 7).

Preferably, the modification at position 184 is a replacement of cysteine to alanine.

According to a particular embodiment, the pro-domain of TNF-α converting enzyme (TACE) comprises a modification in each of the above specified positions. The amino acid sequence of the TACE pro-domain is preferably at least 80%, at least 85%, at least 87%, at least 89%, at least 91%, at least 93%, at least 95% or more say 100% homologous to the TACE pro-domain sequence described in SEQ ID NO: 5 as determined using BlastP software of the National Center of Biotechnology Information (NCBI) using default parameters) and is capable of inhibiting an enzymatic activity of TACE, wherein the percent homology does not include the mutations described herein. In measuring homology between a peptide and a protein of greater size, homology is measured only in the corresponding region; that is, the protein is regarded as only having the same general length as the peptide, allowing for gaps and insertions.

The homolog may also refer to a deletion, insertion, or substitution variant, including an amino acid substitution, thereof and biologically active polypeptide fragments thereof.

Additional modifications and changes can be made in the structure of the TACE pro-domain of the presently disclosed subject matter and still obtain a molecule being capable of inhibiting TACE. For example, certain amino acids can be substituted for other amino acids in a sequence without appreciable loss of peptide activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e. with a biological property of the polypeptide. As detailed in U.S. Pat. No. 4,554,101, the following hydrophilicity values have been assigned to amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); proline (−0.5.+−0.1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine. The presently disclosed subject matter thus contemplates functional or biological equivalents of the TACE pro-domain as set forth above.

Biological or functional equivalents of a polypeptide can be prepared using site-specific mutagenesis according to procedures well known in the art. Accordingly, amino acid residues can be added to or deleted from the TACE pro-domains of the presently disclosed subject matter through the use of standard molecular biological techniques without altering the functionality of the peptide.

According to one embodiment, the amino acid sequence of the pro-domain is modified so as to increase its stability, bioavailability and/or pharmacological efficacy.

In still further aspects, the pro-domain polypeptide may comprise a fusion protein that having a first moiety, which is a pro-domain polypeptide, and a second moiety, which is a heterologous peptide or protein. Fusion proteins may include myc, HA-, or His6-tags. Fusion proteins further include the pro-domain fused to the Fc domain of a human IgG. In particular aspects, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130. The Fc moiety can be derived from mouse IgG1 or human IgG2$_M$4. Human IgG2$_M$4 (See U.S. Published Application No. 20070148167 and U.S. Published Application No. 20060228349) is an antibody from IgG2 with mutations with which the antibody maintains normal pharmacokinetic profile but does not possess any known effector function.

Exemplary amino acid sequences of a pro-domain fused to an Fc domain is set forth in SEQ ID NO: 9 and SEQ ID NO: 10.

Fusion proteins further include the pro-domain fused to human serum albumin, transferrin, or an antibody.

In further still aspects, the pro-domain is conjugated to a carrier protein such as human serum albumin, transferrin, or an antibody molecule.

The term "polypeptide" as used herein refers to a polymer of natural or synthetic amino acids, encompassing native peptides (either degradation products, synthetically synthesized polypeptides or recombinant polypeptides) and peptidomimetics (typically, synthetically synthesized peptides), as well as peptoids and semipeptoids which are polypeptide analogs, which may have, for example, modifications rendering the polypeptides even more stable while in a body or more capable of penetrating into cells.

Such modifications include, but are not limited to N terminus modification, C terminus modification, polypeptide bond modification, including, but not limited to, CH2-NH, CH2-S, CH2-S═O, O═C—NH, CH2-O, CH2-CH2, S═C—NH, CH═CH or CF═CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Polypeptide bonds (—CO—NH—) within the polypeptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH═CH—), retro amide bonds (—NH—CO—), polypeptide derivatives (—N(R)—CH2-CO—), wherein R is the "normal" side chain, naturally presented on the carbon atom.

These modifications can occur at any of the bonds along the polypeptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the polypeptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids (stereoisomers).

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| Alanine | Ala | A |
| Arginine | Arg | R |

TABLE 1-continued

| Amino Acid | Three-Letter Abbreviation | One-letter Symbol |
|---|---|---|
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Iie | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-Carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-Carboxylate | Norb | L-N-methylglutamine | Nmgin |
|  |  | L-N-methylglutamic acid | Nmglu |
| Cyclohexylalanine | Chexa | L-N-methylhistidine | Nmhis |
| Cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α ethylcyclohexylalanine | Mchexa |
| D-α-methylarginine | Dmarg | α-methylcyclopentylalanine | Mcpen |
| D-α-methylasparagine | Dmasn | α-methyl-α-naphylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl)glycine | Nhtrp |
| D-N-methyllysine | Dnmlys | N-methyl-y-aminobutyrate | Nmgabu |
| N-methylcyclohexylalanine | Nmchexa | D-N-methylmethionine | Dnmmet |
| D-N-methylornithine | Dnmorn | N-methylcyclopenylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |

TABLE 2-continued

| Non-conventional amino acid | Code | Non-conventional amino acid | Code |
|---|---|---|---|
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | Penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-r-butylglycine | Mtbug |
| L-α-methylcysteine | Mcys | L-methylethylglycine | Metg |
| L-α thylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N- methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | Penicillamine | Pen |
| L-homophenylalanine | Hphe | L-α-methylalanine | Mala |
| L-α-methyl arginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α ethylhistidine | Mhis | L- α-methylhomophenylalanine | Mhphe |
| L-α thylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α ethylvaline | Mtrp | L-α-methyltyrosine | Mtyr |
| L-α-methylleucine | Mval | L-N-methylhomophenylalanine | Nmhphe |
|  | Nnbhm |  |  |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc |  |  |

Recombinant techniques are typically used to generate the pro-domain polypeptides of the present invention. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

To produce a polypeptide of the present invention using recombinant technology, a polynucleotide encoding the pro-domain polypeptide of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

As mentioned hereinabove, polynucleotide sequences of the present invention are inserted into expression vectors (i.e., a nucleic acid construct) to enable expression of the recombinant polypeptide. The expression vector of the present invention may include additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals). It will be appreciated that the expression vector may also comprise polynucleotide sequences encoding other polypeptides that are transcriptionally linked to the nuclear targeting peptides of the present invention. Such polypeptides are further described herein below.

Promoters used in the expression vectors may be constitutive or inducible. Tissue specific promoters are also contemplated.

A variety of prokaryotic or eukaryotic cells can be used as host-expression systems to express the peptides of the present invention. These include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

According to this embodiment of this aspect of the present invention, the nucleic acid sequence encoding the pro-domain polypeptides of the present invention may be altered, to further improve expression levels in the expression system (e.g. bacterial expression system). Thus the polynucleotide sequence encoding the pro-domain may be modified in accordance with the preferred codon usage for bacteria. Thus, increased expression of the pro-domain polypeptides in particular systems may be obtained by utilizing a modified or derivative nucleotide sequence. Examples of such sequence modifications include, but are not limited to, an altered G/C content to more closely approach that typically found in the relevant system, and the removal of codons atypically found in the relevant system commonly referred to as codon optimization.

The phrase "codon optimization" refers to the selection of appropriate DNA nucleotides for use within a structural gene or fragment thereof that approaches codon usage within the relevant system.

Examples of polynucleotide sequences that may be used to express the pro-domains of the present invention are provided in SEQ ID NOs: 11-16.

The present inventors have shown that using a bacterial expression system, it is possible to generate a recombinant TACE pro-domain which is expressed in the cytosol and not in inclusion bodies. The TACE pro-domain was soluble and folded correctly so that no additional folding step was required for its isolation.

It will be appreciated that the polynucleotides of the present invention may also be expressed directly in the subject (i.e. in vivo gene therapy) or may be expressed ex vivo in a cell system (autologous or non-autologous) and then administered to the subject. Gene therapy techniques are further described hereinbelow.

Other than containing the necessary elements for the transcription and translation of the inserted coding sequence (encoding the polypeptide), the expression construct of the present invention can also include sequences engineered to optimize stability, production, purification, yield or activity of the expressed peptide.

Various methods can be used to introduce the expression vector of the present invention into the host cell system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Depending on the vector and host system used for production, resultant peptides and/or polypeptides of the present invention may either remain within the recombinant cell, secreted into the fermentation medium, secreted into a space between two cellular membranes, such as the periplasmic space in *E. coli*; or retained on the outer surface of a cell or viral membrane.

Following a predetermined time in culture, recovery of the recombinant peptide and/or polypeptide is effected.

The phrase "recovering the recombinant polypeptide" used herein refers to collecting the whole fermentation medium containing the polypeptide and need not imply additional steps of separation or purification.

Thus, pro-domain polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide of the present invention and fused cleavable moiety. Such a fusion protein can be designed so that the polypeptide can be readily isolated by affinity chromatography; e.g., by immobilization on a column specific for the cleavable moiety. Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

Exemplary purification tags for purposes of the invention include but are not limited to polyhistidine, V5, myc, protein A, gluthatione-S-fransferase, maltose binding protein (MBP) and cellulose-binding domain (CBD) [Sassenfeld, 1990, TIBTECH, 8, 88-9]. In the case of CBD fusion proteins, the pro-domain polypeptides are fused to a substrate-binding region of a polysaccharidase (cellulases, chitinases and amylases, as well as xylanases and the beta.-1,4 glycanases). The affinity matrix containing the substrate such as cellulose can be employed to immobilize the pro-domain polypeptides. The pro-domain polypeptides can be removed from the matrix using a protease cleavage site.

An exemplary polyhistidine tag sequence together with a protease site is provided in SEQ ID NO: 18.

An exemplary pro-domain amino acid sequence comprising a polyhistidine tag is set forth in SEQ ID NO: 17.

The polypeptides of the present invention are preferably retrieved in "substantially pure" form.

As used herein, the phrase "substantially pure" refers to a purity that allows for the effective use of the protein in the applications described herein.

The pro-domain of some embodiments of the invention may be chemically modified following expression for increasing bioavailability.

Thus for example, the present invention contemplates modifications wherein the pro-domain polypeptide is linked to a polymer. The polymer selected is usually modified to have a single reactive group, such as an active ester for acylation or an aldehyde for alkylation, so that the degree of modification may be controlled. Included within the scope of polymers is a mixture of polymers. Preferably, for therapeutic use of the end-product preparation, the polymer will be pharmaceutically acceptable.

The polymer or mixture thereof may be selected from the group consisting of, for example, polyethylene glycol (PEG), monomethoxy-polyethylene glycol, dextran, cellulose, or other carbohydrate based polymers, poly-(N-vinyl pyrrolidone)polyethylene glycol, propylene glycol homopolymers, a polypropylene oxide/ethylene oxide co-polymer, polyoxyethylated polyols (for example, glycerol), and polyvinyl alcohol.

In further still embodiments, the pro-domain polypeptide is modified by PEGylation, HESylation CTP (C terminal peptide), crosslinking to albumin, encapsulation, modification with polysaccharide and polysaccharide alteration. The modification can be to any amino acid residue in the pro-domain polypeptide.

According to one embodiment the modification is to the N or C-terminal amino acid of the pro-domain polypeptide. This may be effected either directly or by way coupling to the thiol group of a cysteine residue added to the N or C-terminus or a linker added to the N or C-terminus such as Ttds. In further embodiments, the N or C-terminus of the pro-domain polypeptide comprises a cysteine residue to which a protecting group is coupled to the N-terminal amino group of the cysteine residue and the cysteine thiolate group is derivatized with a functional group such as N-ethylmaleimide, PEG group, HESylated CTP.

It is well known that the properties of certain proteins can be modulated by attachment of polyethylene glycol (PEG) polymers, which increases the hydrodynamic volume of the protein and thereby slows its clearance by kidney filtration. (See, for example, Clark et al., J. Biol. Chem. 271: 21969-21977 (1996). Therefore, it is envisioned that the core peptide residues can be PEGylated to provide enhanced therapeutic benefits such as, for example, increased efficacy by extending half-life in vivo. Thus, PEGylating the pro-domain polypeptide will improve the pharmacokinetics and pharmacodynamics of the pro-domain polypeptide.

PEGylation methods are well known in the literature and described in the following references, each of which is incorporated herein by reference: Lu et al., Int. J. Pept. Protein Res. 43: 127-38 (1994); Lu et al., Pept. Res. 6: 140-6 (1993); Felix et al., Int. J. Pept. Protein Res. 46: 253-64 (1995); Gaertner et al., Bioconjug. Chem. 7: 38-44 (1996); Tsutsumi et al., Thromb. Haemost. 77: 168-73 (1997); Francis et al., Int. J. Hematol. 68: 1-18 (1998); Roberts et al., J. Pharm. Sci. 87: 1440-45 (1998); and Tan et al., Protein Expr. Purif. 12: 45-52 (1998). Polyethylene glycol or PEG is meant to encompass any of the forms of PEG that have been used to derivatize other proteins, including, but not limited to, mono-(C.sub.1-10)alkoxy or aryloxy-polyethylene glycol. Suitable PEG moieties include, for example, 40 kDa methoxy poly(ethylene glycol) propionaldehyde (Dow, Midland, Mich.); 60 kDa methoxy poly(ethylene glycol) propionaldehyde (Dow, Midland, Mich.); 40 kDa methoxy poly(ethylene glycol) maleimido-propionamide (Dow, Midland, Mich.); 31 kDa alpha-methyl-w-(3-oxopropoxy), polyoxyethylene (NOF Corporation, Tokyo); mPEG.sub.2-NHS-40 k (Nektar); mPEG$_2$-MAL-40 k (Nektar), SUNBRIGHT GL2-400MA ((PEG).sub.240 kDa) (NOF Corporation, Tokyo), SUNBRIGHT ME-200MA (PEG20 kDa) (NOF Corporation, Tokyo). The PEG groups are generally attached to the pro-domain polypeptide via acylation, amidation, thioetherification or reductive alkylation through a reactive group on the PEG moiety (for example, an aldehyde, amino, carboxyl or thiol group) to a reactive group on the pro-domain polypeptide (for example, an aldehyde, amino, carboxyl or thiol group).

The PEG molecule(s) may be covalently attached to any Lys or Cys residue at any position in the pro-domain polypeptide. Other amino acids that can be used are Tyr and His. Optional are also amino acids with a Carboxylic side chain. The pro-domain polypeptide described herein can be PEGylated directly to any amino acid at the N-terminus by way of the N-terminal amino group. A "linker arm" may be added to the pro-domain polypeptide to facilitate PEGylation. PEGylation at the thiol side-chain of cysteine has been widely reported (See, e.g., Caliceti & Veronese, Adv. Drug Deliv. Rev. 55: 1261-77 (2003)). If there is no cysteine residue in the pro-domain polypeptide, a cysteine residue can be introduced through substitution or by adding a cysteine to the N-terminal amino acid. Other options include reagents that add thiols to polypeptides, such as Traut's reagents and SATA.

In particular aspects, the PEG molecule is branched while in other aspects, the PEG molecule may be linear. In particular aspects, the PEG molecule is between 1 kDa and 150 kDa in molecular weight. More particularly, the PEG molecule is between 1 kDa and 100 kDa in molecular weight. In further aspects, the PEG molecule is selected from 5, 10, 20, 30, 40, 50 and 60 kDa.

A useful strategy for the PEGylation of pro-domain polypeptide consists of combining, through forming a conjugate linkage in solution, a peptide, and a PEG moiety, each bearing a special functionality that is mutually reactive toward the other. The pro-domain polypeptide can be easily prepared by recombinant means as described above.

According to one embodiment, the PEG is "preactivated" prior to attachment to the pro-domain polypeptide. For example, carboxyl terminated PEGs may be transformed to NHS esters for activation making them more reactive towards lysines and N-terminals.

According to another embodiment, the pro-domain polypeptide is "preactivated" with an appropriate functional group at a specific site. Conjugation of the pro-domain polypeptide with PEG may take place in aqueous phase or organic co-solvents and can be easily monitored by SDS-PAGE, isoelectric focusing (IEF), SEC and mass spectrometry. The PEGylated pro-domain polypeptide is then purified. Small PEGs may be removed by ultra-filtration. Larger PEGs are typically purified using anion chromatography, cation chromatography or affinity chromatography. Characterization of the PEGylated polypeptide may be carried out by analytical HPLC, amino acid analysis, IEF, analysis of enzymatic activity, electrophoresis, analysis of PEG:protein ratio, laser desorption mass spectrometry and electrospray mass spectrometry.

Removal of excess free PEG may be performed by packing a column (Tricorn Empty High-Performance Columns, GE Healthcare) with POROS 50 HQ support (Applied Biosystems), following which the column is equilibrated with equilibration buffer (25 mM Tris-HCl buffer, pH 8.2). The PEGylated pro-domain is loaded onto the equilibrated column and thereafter the column is washed with 5CV of equilibration buffer. Under these conditions, the pro-domain binds to the column. PEGylated pro-domain is eluted in the next step by the elution buffer (0.3M NaCl, 25 mM Tris-HCl buffer, pH 8.2). The peak of this stage may be pooled and stored at 2-8° C. for short term, or frozen at −20° C. for long term storage.

As mentioned hereinabove, the polynucleotides of the present invention may also be administered directly into a subject where it is translated in the target cells i.e. gene therapy.

Gene therapy as used herein refers to the transfer of genetic material (e.g. DNA or RNA) of interest into a host to treat or prevent a genetic or acquired disease or condition or phenotype. The genetic material of interest encodes a product (e.g. a protein, polypeptide, peptide, functional RNA, antisense) whose production in vivo is desired. For example, the genetic material of interest can encode a hormone, receptor, enzyme, polypeptide or peptide of therapeutic value. For review see, in general, the text "Gene Therapy" (Advanced in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ. The cells may be autologous or non-autologous to the subject. Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

In in vivo gene therapy, target cells are not removed from the subject, rather the genetic material to be transferred is introduced into the cells of the recipient organism in situ, that is within the recipient. In an alternative embodiment, if the host gene is defective, the gene is repaired in situ (Culver, 1998. (Abstract) Antisense DNA & RNA based therapeutics, February 1998, Coronado, Calif.).

These genetically altered cells have been shown to express the transfected genetic material in situ.

To confer specificity, preferably the nucleic acid constructs used to express the peptides and/or polypeptides of the present invention comprise cell-specific promoter sequence elements, such as cancer specific promoters (e.g. survivin promoter—Chen et al, Cancer Gene Therapy, 2004, Volume 11, Number 11, Pages 740-747).

For gene therapy, nucleic acids are typically introduced into cells by infection with viral agents. This is because higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As illustrated in Example 1, the present inventors have shown that the TACE pro-domains of the present invention may be used to treat an irritable bowel disease.

Inflammatory bowel diseases (IBD) are severe gastrointestinal disorders characterized by intestinal inflammation and tissue remodeling, that increase in frequency and may prove disabling for patients. The major forms of IBD, ulcerative colitis (UC) and Crohn's disease are chronic, relapsing conditions that are clinically characterized by abdominal pain, diarrhea, rectal bleeding, and fever.

The present inventors contemplate that the TACE pro-domains may be used to treat other inflammatory disorders.

Thus, according to another aspect of the present invention there is provided a method of treating an inflammatory disease, the method comprising administering to the subject a therapeutically effective amount of a polypeptide comprising a pro-domain of TNF-α converting enzyme (TACE), the polypeptide being devoid of a catalytic domain of the TACE, the polypeptide comprising a modification at $R^{58}$ which renders the polypeptide resistant to furin degradation the polypeptide being capable of downregulating an activity of TACE, thereby treating the inflammatory disease.

Preferred individual subjects according to the present invention are animals such as mammals (e.g., canines, felines, ovines, porcines, equines, bovines, primates) preferably, humans.

Below is a list of inflammatory diseases that the present inventors contemplate treating with the pro-domains described herein.

Inflammatory diseases—include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Bane syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12): 2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 December 29; 830:266), skin diseases, cutaneous diseases, dermal diseases, bullous skin diseases, *pemphigus vulgaris*, bullous pemphigoid and *pemphigus foliaceus*.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Autoimmune diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl:S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, *pemphigus vulgaris*, bullous pemphigoid and *pemphigus foliaceus*.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Bane syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Cancerous Diseases

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

Additional contemplated diseases that may be treated with the pro-domain described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes, Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), *Pemphigus*, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, *Scleroderma*, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, Wegener's granulomatosis (now termed Granulomatosis with Polyangiitis (GPA).

The TACE pro-domains or expression constructs encoding same of the present invention can be provided to the treated subject (i.e. mammal) per se (e.g., purified or directly as part of an expression system) or can be provided in a pharmaceutical composition comprising the pro-domain of the present invention. As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the recombinant TACE pro-domain (or polynucleotide encoding same) of the present invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable peripheral routes of administration may, for example, include oral, rectal, transmucosal, especially transnasal, intestinal or parenteral delivery, including intramuscular, subcutaneous and intravenous, intraperitoneal, intranasal, or intraocular injections.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran.

Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (nucleic acid construct) effective to prevent, alleviate or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an U.S. Food and Drug Administration (FDA) approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration (FDA) for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989);

Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Therapeutic Effect of TACE Pro-Domain in Inflammation Bowel Disease Model

Materials and Methods
TACE Pro-Domain Construct

The construction of the pET28 TACE pro-domain was performed by removing the catalytic domain from the pET28 pro-cat TACE construct. The pET28 pro-cat is a synthetic gene generated for codon usage in *E. coli* and it was cloned into the KpnI-BamHI of the pET28-TevH with following primers:

```
sTACEKpnIF
                              (SEQ ID NO: 1)
TCACGGTACCGACCCGGGCTTTGGCCCG sTACEBamHIR
                              (SEQ ID NO: 2)
GCTCGGATCCTCAAACTTTGTTGCTACGTTCCTGAA
```

The removal of the catalytic domain was performed by inverse PCR using two primers:

```
DelCatF
               (5' phosphorylated; SEQ ID NO: 3)
TGAGGATCCGAATTCGAGCTCCG DelCatR
                              (SEQ ID NO: 4)
ACGTTTCACACGATGCACCAGTTC.
```

Following the reaction and DpnI treatment the linear PCR product was ligated prior to transformation. The sequence of the pro-TACE is as set forth in SEQ ID NO: 5.

Expression and Purification of TACE Pro-Domain

*E. coli* BL21(DE3) electrocompetent cells were transformed with the corresponding TACE pro-domain plasmid and plated on LB plates containing 30 µg/ml Kanamicin. After overnight incubation at 37° C., the cells were resuspended in 1 liter of LB with 30 µg/ml Kanamicin. The cells were grown at 37° C., induced with 200 µM isopropyl-β-D-thiogalactopyranoside at an optical density of 0.6 and harvested after overnight induction at 15° C. The cell pellets were resuspended with 50 mM Tris, pH 8, 300 mM NaCl, 20 mM Immidazole, 0.1 mg/ml Lysozyme, 1 µg/ml DNAse and 1 pill of Inhibitor protease cocktail, following which they were sonicated and centrifuged at 15000 rpm for 45 minutes at 4° C. The supernatant was applied to a 5-ml Ni+2 column. The column was washed with 50 mM Tris, pH 8, 300 mM NaCl, and 20 mM imidazole. The protein was eluted with 50 mM Tris, pH 8, 300 mM NaCl, and 250 mM imidazole. The eluted protein was dialyzed against 50 mM Tris, pH 8 at 4° C. overnight and applied to HiTrap Q HP column. The column was washed with 50 mM Tris, pH 8 and elution was done with a gradient against the same buffer containing 1M NaCl. Fractions were collected analyzed in 12% SDS PAGE. The fractions containing the TACE pro-domain were concentrated by Vivaspin with 10,000 MW cutoff to the desired concentration. The expression of the pro domain in this construct is in a native soluble form, in contrast to previous reports [Gonzales, P. E., et al., J Biol Chem, 2004. 279(30): p. 31638-45; Li et al., Int J Mol Sci. 2009 December; 10(12): 5442-5454], where the expression was performed in inclusion bodies followed by a refolding step. The previous variant of the refolded TACE pro-domain could not exist at concentrations higher than 0.09-0.14 mg/ml after refolding, whereas the soluble pro domain could be concentrated to higher concentration for animal studies purposes.

Activity Assay, Inhibition by TACE Pro-Domain

The catalytic activities were tested by hydrolysis processing of flouregenic substrate by catalytic domains of TACE (Mca-PLAGAV-Dpa-RSSSR), MMP9, MMP7 and MT1-MMP (Mca-PLGL-Dpa-AR) at 37° C. monitoring the increasing flourescence intensity at Emission=340 and Excitation=400. The reactions were done in a flouregenic buffer containing 50 mM Tris, pH 8, 150 mM NaCl, 5 µM $ZnCl_2$ and 0.05% Brij-35, enzyme concentrations were: 10 nM TACE, 1 nM MMP9, 10 nM MMP7 and 5 nM MT1-MMP. The inhibition assay by TACE pro-domain was carried out in ascending concentration of pro domain after pre-incubation in 37° C. for 30 min.

Inhibition in Cell Based Assays

Primary macrophages were extracted from the peritoneum 4 days after Thioglycollate injection in BALB/c mice and 50,000 cell/well in 96 wells were seeded in DMEM without serum. The cells were incubated with 100 ng LPS and different concentrations of TACE pro-domain or 20 mM TAPI in DMEM media for 3 hours and TNF-α was measured with Thermo mouse TNF-α ELISA kit. 1,000 CHO cells stably transfected with human TNF-α were seeded overnight in 96 well and pre-incubated 2 hours with mentioned concentration of TACE pro-domain and TAPI then the media was washed and replaced with fresh media containing the same substances. Media were collected after 4 hours and TNF-α was measured with Thermo human TNF-α ELISA kit.

Induction of TNBS Colitis and Treatment with TACE Pro-Domain

TNBS colitis was induced in female balb/c mice ages 8-10 weeks as described [2], control mice received 50% ethanol alone. TACE pro-domain were injected intravenously daily for 7 days at 1 and 4 mg/kg, starting from day 0 (TNBS administration). As negative control mice were treated with vehicle PBS and positive control were treated with Dexa. Each treatment group contained 10 mice. Macroscopic scoring of gross colonic damage, 7 days after TNBS administration was graded in a blinded fashion according to Reuter et al. [3]. Microscopic scoring: proximal, medial, and distal portions of colon were fixed in 10% phosphate-buffered formalin. Paraffin-embedded sections were stained with hematoxylin and eosin. The degree of histologic damage and inflammation was graded in a blinded fashion according to Elson et al. [4]. All animal studies were approved by the Weizmann Animal Care and Use Committee.

Optical Imaging of Fresh Tissues

TACE pro-domain was conjugated to AnaTag Hilyte Fluor 750 (AnaSpec) according to manufacturer's instruction. TNBS colitis induced mice were injected via tail vein with 1.5 nmol of TACE pro-domain-HiLyte Fluor 750 (4.5 nmol equivalent Hilyte Fluor 750/mouse) or 4.5 nmol of Hilyte Fluor 750 only. One TNBS treated mouse was not injected and was used as a blank control. One group of mice sacrificed at 2 hours and the other group of mice was sacrificed at 10 hours after intravenous injection of fluorescent marker tagged TACE pro-domain and fluorescent marker only. The dissected tissues (Heart, Lung, Kidney, Liver, Stomach, Spleen, Intestine, Colon) were imaged immediately. The mean fluorescent intensity of each tissue sample was obtained by subtracting the mean fluorescent intensity of corresponding tissue from the blank mouse. The fluorescent intensities in the heart were used to reflect the fluorescent intensities in the blood. The colon to heart ratio of fluorescence was calculated. Fluorescence imaging was performed with an IVIS (IVIS®100/XFO-12, Xenogen Corp., Alameda, Calif., USA). Near Infrared Fluorescence, in units of photons/sec, was detected using 710/50 nm and 800/75 nm filter sets for excitation and emission, respectively, with one second integration time.

Results

To examine the selectivity of TACE pro-domain towards TACE, the in vitro inhibition activity of different members of the MMP family was tested by monitoring the cleavage of flouregenic substrate. TACE, MMP7, MT1-MMP and MMP9 catalytic domain shares a similar topology (FIG. 3), however, inhibition studies using TACE pro-domain shows selective inhibition to TACE. $IC_{50}$ values of TACE pro-domain inhibition towards TACE is about 119 nM, whereas, towards MMP9 is 40 fold higher, MMP7 is 80 fold higher and in the case of MT1-MMP it was not possible to determine (FIGS. 6A-B). This result indicates that besides the metal chelation of the active Zn(II), the inhibition also involved a specific protein-protein inhibition presented in TACE pro-domain which is most compatible towards TACE catalytic domain.

TNF-α is produced chiefly by activated macrophages although other cell types can produce it as well. Initially, the inhibitory activity of TACE pro-domain was tested in a cell-based assay using two type of cell lines—CHO cells stably transfected with human TNF-α and primary macrophages harvested from balb/c mice. The TACE pro-domain exhibited an inhibitory effect in a dose dependent manner in CHO cells. A concentration of 5 µM reduced secretion of TNF-α by 5 fold as compared to no treatment. Furthermore, no significant effect was found at concentrations as low as 0.3125 µM (FIG. 7A). Stimulation with 1 µg/ml LPS is required for TNF-α secretion in primary macrophages cells. It causes a 50- to 60-fold increase in TNF-α compared to resting cells. Treatment with TACE pro-domain prevented TNF-α secretion by 6-7 fold at the highest concentration (1 µM). This effect was reduced as the level of pro-domain was decreased. At 0.25 µM, no reduction in TNF-α secretion was found (FIG. 7B).

To evaluate the therapeutic potency of TACE pro-domain in autoimmune disease, an inflammatory bowel disease mouse model induced by TNBS/ethanol administration was used. TNBS is believed to haptenize colonic autologous or microbiota proteins rendering them immunogenic to the host immune system. This model is useful to study T helper cell-dependent mucosal immune responses. Mice subjected to intrarectal administration of TNBS developed severe illness with anticipated symptoms such as bloody diarrhea and severe weight loss up to 16%, resulting in mortality of 40% (FIGS. 8A, B). Mice treated with 1 mg/kg and 4 mg/kg daily injections of the TACE pro-domain exhibited lower mortality of 20% and 10% respectively and lower weight loss of 15%-14% (FIGS. 8A, B). The efficacy of the pro-domain was also apparent through an improvement in the macroscropic and histological scores (FIGS. 8C, D). The TACE pro-domain treated mice displayed a longer colon length, solid feces and fewer lesions (FIG. 8E). Moreover, the treatment also prevented massive infiltration of macrophages and immune cells to the colon lumen as seen in the PBS control (FIG. 8F). Overall, these results indicate that the inhibitory TACE pro-domain have a considerable efficacy in T helper cell-dependent IBD disease states. This is likely caused by the prevention of secreted TNF-α in the inflammation focal arresting the development of inflammation processes.

To explore er the TACE pro-domain reached the inflamed colon, fluorescence imaging of fresh tissues was performed using HiLyte Fluor 750 labeled pro-domain. FIGS. 9A-C demonstrates that pro-domain could be detected from 10 hours after intravenous administration, in the colon of TNBS-treated mice located in focal patches along the colon (FIGS. 9A, B). The fluorescent dye itself can also be detected in the colon, which can be explained by the high vasculature permeability of inflamed colon associated with colitis, shown recently by high-resolution MRI studies. In contrast to the control experiments with the fluorescent dye, where the dye diffused throughout the colon, there was significant accumulation of fluorescently labeled pro-domain 10 hrs after administration in focal inflammatory-like patches (FIG. 9B).

This suggests the pro-domain demonstrates specificity against the activated immune cells in the region of lesion. The colon/heart ratio indicates the specific accumulation of the pro-domain 2 hours and 10 hours following administration by 4 fold and 16 fold respectively. On the other hand, almost no change was detected when only the fluorescent dye was injected (FIG. 9C).

Example 2

TACE Pro-Domain Modifications

Furin a serine protease is the major convertase responsible for cleavage of TACE pro-domain intracellularly. The TACE pro-domain possesses two different sequences for the recognition of Furin like serine protease. The first is the classical Furin site $R^{211}VKR^{214}/R^{215}$ (SEQ ID NO: 20) between the pro-domain and catalytic domain. The second cleavage site, uncovered by the present inventors, is a non-canonical $R^{56}KR^{58}/D^{59}$ (SEQ ID NO: 22), which, was observed by Hoth et al 2007 as one of the products during the purification of the TACE catalytic domain in insect cells expression system. This second cleavage site does not resemble the well-defined minimal Furin consensus site Arg-X-X-Arg/X (SEQ ID NO: 21). [Molloy, S. S. et. al J. Biol. Chem. 1992, 267, 16396].

According to Nakayama, K. [Biochem J. 1997, 327(Pt 3), 625], other requirements for Furin recognition are:

(i) At the P1 position an Arg is essential;

(ii) In addition to the P1 Arg, at least two out of the three residues at P2, P4, and P6 are required to be basic for efficient cleavage;

(iii) At the P' 1 position, an amino acid with a hydrophobic side chain is not suitable.

The $R^{56}KR^{58}/D^{59}$ (SEQ ID NO: 22) site does not fit in with the basic requirements except for having an Arg at position P1. There are no Arg present at positions P2 (Lys), P4 (Val), and P6 (His) (HSVRKR/D) (SR) ID NO: 23) making it a non-canonical Furin site.

The TACE pro-domain ends with the C-terminus boundary site $R^{211}VKR^{214}/R^{215}$ (sEQ ID NO: 20) that differentiates the pro-domain from the catalytic domain. To stabilize the TACE pro-domain, the present inventors have mutated the $R^{56}KR^{58}/D^{59}$ (SEQ ID NO: 22) site to prevent the processing by protease. The mutation was inserted by switching the Arginine 58 to Alanine namely pro-$R^{58}$A—(amino acid sequence as set forth in SEQ ID NO: 6, polynucleotide sequence as set forth in SEQ ID NO: 12).

To test whether pr-$R^{58}$A is indeed resistant to cleavage by Furin the purified pro-R58A and pro-WT were incubated with Furin. Only pro-WT was processed by Furin generating a smaller fragment of ~17 kDa which corresponds to $D^{58}$-$R^{214}$ after cleavage at $R^{56}KR^{58}/D^{59}$, whereas, pro-$R^{58}$A mutant was not cleaved by Furin (FIG. 10A. The pro-$R^{58}$A mutant inhibits TACE catalytic activity in similar efficiency as the WT, indicating that the mutant is properly folded and fully functional (FIG. 10B).

The Fc region of an antibody assists in proper immune response by binding to Fc receptors, and other immune molecules, such as complement proteins. It mediates different physiological effects including elongation of half-life of proteins in the blood circle, thus FC portion can give an advantage to a given molecule when fused to a protein.

As the present inventors considered utilizing the TACE pro-domain as a therapeutic agent to inhibit TACE activity in vivo, they created an Fc fused molecule. The pro-domain was fused in the C terminus to mouse Fc IgG2a containing the stabilizing $R^{58}$A mutation as mentioned above. Moreover, generating Fc protein requires dimerization of the heavy chain though Cysteines residues, therefore, they mutated the Cysteine embedded in the pro-domain "Cysteine switch" sequence to Serine and preventing misfolding of the whole Fc fused molecule. The fused protein was expressed in HEK 293 mammalian cells in pSEC plasmid containing Ig κ-chain leader sequence for proper folding and essential post translation modifications. The amino acid sequence of the pro-domain polypeptide is as set forth in SEQ ID NO: 9 and the polynucleotide sequence encoding this sequence is as set forth in SEQ ID NO: 15.

The pSEC plasmid containing pro-Fc was transiently transfected with calcium phosphate in HEK 293 and cells were grown 72 hours after in expression media. The medium was collected and subjected to affinity Protein-A column (FIG. 11A). The purified protein was tested for the inhibition of catalytic TACE, and in presents of 500 nM pro-Fc the activity of catalytic TACE is reduced by 25% (FIG. 11B).

In addition, the present inventors created a stable HEK 293 cell line that expresses another pro-Fc. This cell possesses a pro-WT TACE fuse to C terminus Human Fc region. The construct was flanked at the N-terminus by a mouse signal peptide. The amino acid sequence of the pro-domain polypeptide is as set forth in SEQ ID NO: 10 and the polynucleotide sequence encoding this sequence is as set forth in SEQ ID NO: 16. In order to eliminate any possible interaction of TACE pro-domain with Furin protease, the TACE pro-domain was further mutated. Specifically, Arginine 211 was mutated to Alanine and Arginine 214 was mutated to Glycine. In addition, another mutation in the Cysteine 184 to Alanine residue was included. This mutation was previously described by Gonzales 2004 J Biol Chem, 2004. 279(30) as having no different inhibition effect compared to the WT.

In summary, a TACE pro-domain was created having 4 point mutations: $R^{58}$A, $R^{211}$A, $R^{214}$G and $C^{184}$A (referred to herein as 4mut).

Example 3

Therapeutic Effect of TACE Pro-Domain 4mut in a LPS Septic Shock Model

In order to evaluate the inhibitory effect of TACE pro-domain and TACE pro-domain 4mut in secretion of TNF-α in vivo, a LPS septic shock model was applied. Septic shock is a medical condition that is a result of severe infection and sepsis, followed by a systemic inflammation condition, which may cause multiple organ failure and death. Most cases of septic shock are caused by endotoxin producing Gram-negative bacilli lipopolysaccharides (LPS). During septic and endotoxic shocks, homeostasis is completely lost, inflammation dominates over anti-inflammatory pathways, and coagulation dominates over fibrinolysis. TNF-α plays a major role as a pro-inflammatory mediator and, during septic shock; its levels are elevated, triggering the initiative overwhelming immune response. Injection of endotoxin (LPS) has been used to mimic the septic response in animal models.

Materials and Methods

In brief, C57/BL mice were injected with TACE pro-domain or PBS control 1 hour prior to 100 mg LPS injection. Blood was collected 1.5 hour after LPS injection and TNF-α level in serum was detected by standard ELISA kit.

Results

Systemic TNF-α was elevated in PBS control (~3000 pg/ml) compared to the naïve mice where TNF-α was undetectable. The treatment of WT TACE pro-domain reduced TNF-α levels to ~600 pg/ml when administered at a concentration of 1 mg/kg, but no reduction of TNF-α was observed when administered at a concentration of 4 mg/kg. Surprisingly, treatment with the 4mut TACE pro-domain exhibits higher reduction levels in serum TNF-α at both concentrations: ~400 pg/ml for 4mut TACE pro-domain 1 mg/kg and ~350 pg/ml for 4mut TACE pro-domain 4 mg/kg (FIG. 12). This experiment proves that TACE pro-domain is an effective modulator of TNF-α secretion in vivo and that the 4mut TACE pro-domain, possesses an increase therapeutic efficacy in reducing TNF-α in LPS septic shock in vivo model as compared to the WT TACE pro-domain.

Example 4

TACE Pro-Domain in Collagen Induced Arthritis In Vivo Mouse Model

The efficacy of TACE pro-domain to treat arthritis was evaluated in a semi-therapeutic murine collagen induced arthritis (CIA) model. Treatment with TACE pro-domain begun when 40% of the animals developed signs of disease.
Materials and Methods
DBA/1LacJ male mice were immunized on day 0 with 100 μg of bovine type II collagen in CFA, and the mice were boosted with 100 μg of bovine type II collagen on day 21. Treatment with either TACE pro-domain or a vehicle control began at day 23 at a dose of 3 mg/kg.
Results
As demonstrated in FIGS. 13A-C, 10-day treatment with TACE pro-domain resulted in a long-term therapeutic effect that was significantly different from that in the control group through the entire study period up to 18 days (8 days following the end of treatment). Mice treated with TACE pro-domain displayed a significantly lower arthritis severity index score (A), histological score (B), as well as lowered serum antibodies specific to type II collagen in a concentration-dependent manner (C).

Example 5

Treatment of Subject with Inflammatory Bowel Disease, Crohn's Disease with 4mut TACE Pro-Domain Placebo-controlled study to evaluate the safety, tolerability, and efficacy of 4mut TACE pro-domain is assessed in a clinical trial of patients with symptoms of Crohn's disease, patients with mild to moderate active Crohn's disease will improve their symptoms of Crohn's disease and quality of life. Primary Outcome Measures: number of Participants who had remission of Crohn's Disease After 10-week Treatment [Time Frame: Baseline to 10 weeks] Remission is defined by a Crohn's Disease Activity Index (CDAI) score of ≤150. That is, if a participant had 150 or less of CDAI score after 8-week treatment, the participant had the remission of Crohn's disease. Another Outcome Measures: Number of Participants Who Had Remission of Crohn's Disease After 2-week Treatment. The number of participants who had remission of Crohn's disease (i.e., same CDAI score ≤150) after 2-week, after 4-week, or after 6-weeks treatment. Statistical analysis may be done by Kaplan-Miere method. Change in CDAI Score From Baseline to 8 Weeks [Time Frame: Baseline to 8 weeks].

The patients receive doses of IV 4mut TACE pro-domain over 8 weeks to 8 treatments, at dosage levels of, e.g., 0 (placebo group), 10 and 100 mg. It is noted that other dosing, intervals and frequencies and dosage levels and formulations may be useful for improving CDAI score of ≤150, reducing rate of progression or halt progression, and optionally for prevention or reducing the risk of progression.

Example 6

Treatment of Subject with Ulcerative Colitis (UC), with 4mut TACE Pro-Domain

Subject has a documented diagnosis of mild to moderate Ulcerative Colitis Study to evaluate the efficacy by the frequency and severity of adverse events is assessed in a clinical trial of patients with symptoms of Ulcerative Colitis disease after treatment with 4mut TACE pro-domain over 8 weeks, as demonstrated clinically and by endoscopy. Patients subjects will have a documented history of ulcerative colitis, and a modified UCDAI score of 4-10, rectal bleeding score of 1 or more (based on subject diary), and mucosal appearance score (based on endoscopy) of 1 point or more at baseline. Primary Outcome Measures: Change from baseline in the modified Ulcerative Colitis Disease Activity Index (modified UCDAI) score at the end of the 8 week treatment period.

The patients receive doses of IV 4mut TACE pro-domain over 8 weeks of 8 treatments, at dosage levels of, e.g., 0 (placebo group), 10, and 100 mg. It is noted that other dosing, intervals and frequencies and dosage levels and formulations may be useful for improving UCDAI score, and optionally for prevention or reducing the risk of progression.

Example 7

Treatment of Subject with Septic Shock, with 4mut TACE Pro-Domain

Study to evaluate the effects of 4mut TACE pro-domain on microcirculation and organ function for septic shock. The trial will enroll patients with suspected or documented site of infection and having 2 out of the three Systemic Inflammatory Response Syndrome (SIRS) criteria. Patients will also be receiving standard of care, Placebo comparator. Early-goal directed therapy including but not limited to fluid resuscitation, appropriate and early antibiotics, source control and evaluation for drotrecogin alpha where deemed appropriate, while being supported for septic shock.

In all groups, norepinephrine will be titrated to achieve a mean arterial pressure (MAP) between 65 and 75 mmHg Data from right heart catheterization, from microcirculation (SDF imaging) and from organ function as well as norepinephrine requirements will be obtained at baseline and after 24, 48, 72 hours.

The patients receive single doses of IV 4mut TACE pro-domain over first 24 hours, at dosage levels of, e.g., 0 (placebo group), 10, and 100 mg. It is noted that other dosing, intervals and frequencies and dosage levels and formulations may be useful for improving systemic hemodynamics, microcirculation and organ function.

Example 8

Treatment of Subject with Rheumatoid Arthritis with 4mut TACE Pro-Domain

Study to evaluate the efficacy of 4mut TACE pro-domain in Rheumatoid Arthritis. Patients subjected will be defined with Rheumatoid Arthritis onset at >16 years, with total disease duration of at least 6 months. The patients will receive doses of IV 4mut TACE pro-domain over 8 weeks of 8 treatments, at dosage levels of, e.g., 0 (placebo group), 10, and 100 mg. The modified Disease Activity Score (DAS28) will be the primary outcome measure. It is noted that other

Example 9

Treatment of Subject with Systemic Lupus Erythematosus with 4mut TACE Pro-Domain A Randomized, Double-Blind, Placebo-Controlled, Study for Treatment of Lupus Nephritis by Inhibition of TACE Using 4mut TACE pro-domain. The trial will enroll patients that meet at least 4 of the 11 American College of Rheumatology (ACR) 1982 Revised Criteria for the Classification of SLE. The patients will receive doses of IV 4mut TACE pro-domain over 8 weeks of 8 treatments, at dosage levels of, e.g., 0 (placebo group), 10, and 100 mg. Outcome Measures: Participant Systematic Lupus Erythematosus Disease Activity Index (SLEDAI) Score at Baseline. It is noted that other dosing, intervals and frequencies and dosage levels and formulations may be useful for improving.

Example 10

Treatment of Subject with Type II Diabetes with 4mut TACE Pro-Domain

The study is a double blind randomized placebo control trial. The objective is to assess therapeutic effects of 4mut TACE pro-domain in the management of type 2 diabetes in an 8 week period. The trial will enroll patients with HbA1c <10%, Hematocrit >34%, Serum creatinine <1.8 mg/dl. Primary Outcome Measures: Glycemic control as measured by HbA1c: Difference in mean reduction between Control and Treatment Groups will be evaluated Secondary Outcome Measures: Device/procedure-related adverse events; hypoglycemic events; Proportion of subjects with HbA1c less than 7.0; reduction of weight for both groups; improvement of glycemic control as measured by HbA1c. The patients will receive doses of IV 4mut TACE pro-domain over 8 weeks of 8 treatments, at dosage levels of, e.g., 0 (placebo group), 10, and 100 mg.

Example 11

The Cysteine 184 to Alanine Mutation Prevented Dimerization of the TACE Pro-Domain in E. Coli Expression System Isolated TACE pro-domain WT and C184A were subjected to SDS PAGE either with reducing sample buffer, containing DTT for reducing disulfide bonds, or non-reducing sample buffer. As expected the TACE pro-domain in reducing buffer presented as a clear band around ~25 kDa. However, in a non-reducing buffer another band appears ~50 kDa indicating formation of a dimer. In contrast, TACE pro-domain C184A mutant shows a single band ~25 kDa corresponding to the monomeric pro-domain either in reducing and non-reducing sample buffer. This result demonstrates the TACE pro-domain C184A mutation prevents dimerization of the protein.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Gonzales, P. E., et al., *Inhibition of the tumor necrosis factor-alpha-converting enzyme by its pro domain.* Journal of Biological Chemistry, 2004. 279(30): p. 31638-31645.
2. Wirtz, S., et al., *Chemically induced mouse models of intestinal inflammation.* Nat Protoc, 2007. 2(3): p. 541-6.
3. Reuter, B. K., et al., *Exacerbation of inflammation-associated colonic injury in rat through inhibition of cyclooxygenase-2.* J Clin Invest, 1996. 98(9): p. 2076-85.
4. Elson, C. O., et al., *Hapten-induced model of murine inflammatory bowel disease: mucosa immune responses and protection by tolerance.* J Immunol, 1996. 157(5): p. 2174-85.

---

What is claimed is:

1. A method of treating an inflammatory disease, the method comprising administering to the subject a therapeutically effective amount of a polypeptide comprising a pro-domain of TNF-α converting enzyme (TACE), said polypeptide being devoid of a catalytic domain of said TACE, said polypeptide comprising a substitution at each of the sites $R^{58}$, $R^{211}$ and $C^{184}$ thereby rendering said polypeptide resistant to furin degradation, said polypeptide being capable of downregulating an activity of TACE, wherein the numbering of the substitution corresponds to the full length human TACE enzyme.

2. The method of claim 1, wherein said inflammatory disease is selected from the group consisting of an autoimmune disease, cancer and hepatitis.

3. The method of claim 2, wherein said autoimmune disease is Crohn's disease or rheumatoid arthritis.

4. The method of claim 1, wherein said substitution at position 211 is a replacement of arginine to alanine, wherein said substitution at position 214 is a replacement of arginine to glycine, and wherein said substitution at position 184 is a replacement of cysteine to alanine.

5. The method of claim 1, wherein said substitution at position 58 is a replacement of arginine to alanine.

6. The method of claim 1, wherein said polypeptide comprises a sequence selected from the group consisting of SEQ ID NOs. 6-8.

* * * * *

SEQUENCE LISTING

```
<160> NUMBER OF SEQ ID NOS: 23

<210> SEQ ID NO 1
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 1
tcacggtacc gacccgggct ttggcccg                                    28

<210> SEQ ID NO 2
<211> LENGTH: 36
<212> TYPE: DNA
<213> ORGANISM: Artificial sequence
<220> FEATURE:
```

<223> OTHER INFORMATION: Single strand DNA oligonucleotide

<400> SEQUENCE: 2
gctcggatcc tcaaactttg ttgctacgtt cctgaa    36

<210> SEQ ID NO 3
<211> LENGTH: 23
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<223> OTHER INFORMATION: 5' phosphorylated

<400> SEQUENCE: 3
tgaggatccg aattcgagct ccg    23

<210> SEQ ID NO 4
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 4
acgtttcaca cgatgcacca gttc    24

<210> SEQ ID NO 5
<211> LENGTH: 192
<212> TYPE: PRT
<213> ORGANISM: Artificial sequence
<220> FEATURE:
<223> OTHER INFORMATION: Non-mutated pro-TACE polypeptide sequence

<400> SEQUENCE: 5

Asp Pro Gly Phe Gly Pro His Gln Arg Leu Glu Lys Leu Asp Ser Leu
1               5                   10                  15

Leu Ser Asp Tyr Asp Ile Leu Ser Leu Ser Asn Ile Gln Gln His Ser
            20                  25                  30

Val Arg Lys Arg Asp Leu Gln Thr Ser Thr His Val Glu Thr Leu Leu
        35                  40                  45

Thr Phe Ser Ala Leu Lys Arg His Phe Lys Leu Tyr Leu Thr Ser Ser
    50                  55                  60

Thr Glu Arg Phe Ser Gln Asn Phe Lys Val Val Val Asp Gly Lys
65                  70                  75                  80

Asn Glu Ser Glu Tyr Thr Val Lys Trp Gln Asp Phe Phe Thr Gly His
                85                  90                  95

Val Val Gly Glu Pro Asp Ser Arg Val Leu Ala His Ile Arg Asp Asp
            100                 105                 110

Asp Val Ile Ile Arg Ile Asn Thr Asp Gly Ala Glu Tyr Asn Ile Glu
        115                 120                 125

Pro Leu Trp Arg Phe Val Asn Asp Thr Lys Asp Lys Arg Met Leu Val
    130                 135                 140

Tyr Lys Ser Glu Asp Ile Lys Asn Val Ser Arg Leu Gln Ser Pro Lys
145                 150                 155                 160

Val Cys Gly Tyr Leu Lys Val Asp Asn Glu Glu Leu Leu Pro Lys Gly
                165                 170                 175

Leu Val Asp Arg Glu Pro Pro Glu Glu Leu Val His Arg Val Lys Arg
            180                 185                 190

<210> SEQ ID NO 6
<211> LENGTH: 192
<212> TYPE: PRT
<213> ORGANISM: Artificial sequence
<220> FEATURE:
<223> OTHER INFORMATION: Pro-TACE, Arg58 to Ala mutated, polypeptide
      sequence

<400> SEQUENCE: 6

```
Asp Pro Gly Phe Gly Pro His Gln Arg Leu Glu Lys Leu Asp Ser Leu
1               5                   10                  15

Leu Ser Asp Tyr Asp Ile Leu Ser Leu Ser Asn Ile Gln Gln His Ser
            20                  25                  30

Val Arg Lys Ala Asp Leu Gln Thr Ser Thr His Val Glu Thr Leu Leu
        35                  40                  45

Thr Phe Ser Ala Leu Lys Arg His Phe Lys Leu Tyr Leu Thr Ser Ser
    50                  55                  60

Thr Glu Arg Phe Ser Gln Asn Phe Lys Val Val Val Asp Gly Lys
65                  70                  75                  80

Asn Glu Ser Glu Tyr Thr Val Lys Trp Gln Asp Phe Phe Thr Gly His
                85                  90                  95

Val Val Gly Glu Pro Asp Ser Arg Val Leu Ala His Ile Arg Asp Asp
            100                 105                 110

Asp Val Ile Ile Arg Ile Asn Thr Asp Gly Ala Glu Tyr Asn Ile Glu
        115                 120                 125

Pro Leu Trp Arg Phe Val Asn Asp Thr Lys Asp Lys Arg Met Leu Val
    130                 135                 140

Tyr Lys Ser Glu Asp Ile Lys Asn Val Ser Arg Leu Gln Ser Pro Lys
145                 150                 155                 160

Val Cys Gly Tyr Leu Lys Val Asp Asn Glu Glu Leu Leu Pro Lys Gly
                165                 170                 175

Leu Val Asp Arg Glu Pro Pro Glu Glu Leu Val His Arg Val Lys Arg
            180                 185                 190
```

<210> SEQ ID NO 7
<211> LENGTH: 192
<212> TYPE: PRT
<213> ORGANISM: Artificial sequence
<220> FEATURE:
<223> OTHER INFORMATION: Pro-TACE, Arg58 to Ala, Arg211 to Ala and
      Arg214 to Gly mutated, polypeptide sequence

<400> SEQUENCE: 7

```
Asp Pro Gly Phe Gly Pro His Gln Arg Leu Glu Lys Leu Asp Ser Leu
1               5                   10                  15

Leu Ser Asp Tyr Asp Ile Leu Ser Leu Ser Asn Ile Gln Gln His Ser
            20                  25                  30

Val Arg Lys Ala Asp Leu Gln Thr Ser Thr His Val Glu Thr Leu Leu
        35                  40                  45

Thr Phe Ser Ala Leu Lys Arg His Phe Lys Leu Tyr Leu Thr Ser Ser
    50                  55                  60

Thr Glu Arg Phe Ser Gln Asn Phe Lys Val Val Val Asp Gly Lys
65                  70                  75                  80

Asn Glu Ser Glu Tyr Thr Val Lys Trp Gln Asp Phe Phe Thr Gly His
                85                  90                  95

Val Val Gly Glu Pro Asp Ser Arg Val Leu Ala His Ile Arg Asp Asp
            100                 105                 110
```

```
Asp Val Ile Ile Arg Ile Asn Thr Asp Gly Ala Glu Tyr Asn Ile Glu
            115                 120                 125

Pro Leu Trp Arg Phe Val Asn Asp Thr Lys Asp Lys Arg Met Leu Val
        130                 135                 140

Tyr Lys Ser Glu Asp Ile Lys Asn Val Ser Arg Leu Gln Ser Pro Lys
145                 150                 155                 160

Val Cys Gly Tyr Leu Lys Val Asp Asn Glu Glu Leu Leu Pro Lys Gly
                165                 170                 175

Leu Val Asp Arg Glu Pro Pro Glu Glu Leu Val His Ala Val Lys Gly
            180                 185                 190
```

<210> SEQ ID NO 8
<211> LENGTH: 192
<212> TYPE: PRT
<213> ORGANISM: Artificial sequence
<220> FEATURE:
<223> OTHER INFORMATION: Pro-TACE, Arg58 to Ala, Arg211 to Ala, Arg214
      to Gly and Cys184 to Ala mutated, polypeptide sequence

<400> SEQUENCE: 8

```
Asp Pro Gly Phe Gly Pro His Gln Arg Leu Glu Lys Leu Asp Ser Leu
1               5                   10                  15

Leu Ser Asp Tyr Asp Ile Leu Ser Leu Ser Asn Ile Gln Gln His Ser
            20                  25                  30

Val Arg Lys Ala Asp Leu Gln Thr Ser Thr His Val Glu Thr Leu Leu
        35                  40                  45

Thr Phe Ser Ala Leu Lys Arg His Phe Lys Leu Tyr Leu Thr Ser Ser
    50                  55                  60

Thr Glu Arg Phe Ser Gln Asn Phe Lys Val Val Val Val Asp Gly Lys
65                  70                  75                  80

Asn Glu Ser Glu Tyr Thr Val Lys Trp Gln Asp Phe Phe Thr Gly His
                85                  90                  95

Val Val Gly Glu Pro Asp Ser Arg Val Leu Ala His Ile Arg Asp Asp
            100                 105                 110

Asp Val Ile Ile Arg Ile Asn Thr Asp Gly Ala Glu Tyr Asn Ile Glu
            115                 120                 125

Pro Leu Trp Arg Phe Val Asn Asp Thr Lys Asp Lys Arg Met Leu Val
        130                 135                 140

Tyr Lys Ser Glu Asp Ile Lys Asn Val Ser Arg Leu Gln Ser Pro Lys
145                 150                 155                 160

Val Ala Gly Tyr Leu Lys Val Asp Asn Glu Glu Leu Leu Pro Lys Gly
                165                 170                 175

Leu Val Asp Arg Glu Pro Pro Glu Glu Leu Val His Ala Val Lys Gly
            180                 185                 190
```

<210> SEQ ID NO 9
<211> LENGTH: 415
<212> TYPE: PRT
<213> ORGANISM: Artificial sequence
<220> FEATURE:
<223> OTHER INFORMATION: Non-mutated pro-TACE fused to an Fc region,
      polypeptide sequence

<400> SEQUENCE: 9

```
Asp Pro Gly Phe Gly Pro His Gln Arg Leu Glu Lys Leu Asp Ser Leu
1               5                   10                  15

Leu Ser Asp Tyr Asp Ile Leu Ser Leu Ser Asn Ile Gln Gln His Ser
            20                  25                  30
```

```
Val Arg Lys Ala Asp Leu Gln Thr Ser Thr His Val Glu Thr Leu Leu
         35                  40                  45

Thr Phe Ser Ala Leu Lys Arg His Phe Lys Leu Tyr Leu Thr Ser Ser
 50                  55                  60

Thr Glu Arg Phe Ser Gln Asn Phe Lys Val Val Val Asp Gly Lys
 65                  70                  75                  80

Asn Glu Ser Glu Tyr Thr Val Lys Trp Gln Asp Phe Phe Thr Gly His
                 85                  90                  95

Val Val Gly Glu Pro Asp Ser Arg Val Leu Ala His Ile Arg Asp Asp
             100                 105                 110

Asp Val Ile Ile Arg Ile Asn Thr Asp Gly Ala Glu Tyr Asn Ile Glu
             115                 120                 125

Pro Leu Trp Arg Phe Val Asn Asp Thr Lys Asp Lys Arg Met Leu Val
130                 135                 140

Tyr Lys Ser Glu Asp Ile Lys Asn Val Ser Arg Leu Gln Ser Pro Lys
145                 150                 155                 160

Val Ser Gly Tyr Leu Lys Val Asp Asn Glu Glu Leu Leu Pro Lys Gly
                165                 170                 175

Leu Val Asp Arg Glu Pro Pro Glu Glu Leu Val His Arg Val Lys Arg
             180                 185                 190

Arg Ala Ala Ala Gln Pro Ala Cys Lys Cys Pro Ala Pro Asn Leu Leu
         195                 200                 205

Gly Gly Pro Ser Val Phe Ile Phe Pro Pro Lys Ile Lys Asp Val Leu
         210                 215                 220

Met Ile Ser Leu Ser Pro Ile Val Thr Cys Val Val Val Asp Val Ser
225                 230                 235                 240

Glu Asp Asp Pro Asp Val Gln Ile Ser Trp Phe Val Asn Asn Val Glu
                245                 250                 255

Val His Thr Ala Gln Thr Gln Thr His Arg Glu Asp Tyr Asn Ser Thr
             260                 265                 270

Leu Arg Val Val Ser Ala Leu Pro Ile Gln His Gln Asp Trp Met Ser
         275                 280                 285

Gly Lys Glu Phe Lys Cys Lys Val Asn Asn Lys Asp Leu Pro Ala Pro
         290                 295                 300

Ile Glu Arg Thr Ile Ser Lys Pro Lys Gly Ser Val Arg Ala Pro Gln
305                 310                 315                 320

Gly Tyr Val Leu Pro Pro Glu Glu Glu Met Thr Lys Lys Gln Val
                325                 330                 335

Thr Leu Thr Cys Met Val Thr Asp Phe Met Pro Glu Asp Ile Tyr Val
                340                 345                 350

Glu Trp Thr Asn Asn Gly Lys Thr Glu Leu Asn Tyr Lys Asn Thr Glu
             355                 360                 365

Pro Val Leu Asp Ser Asp Gly Ser Tyr Phe Met Tyr Ser Lys Leu Arg
         370                 375                 380

Val Glu Lys Lys Asn Trp Val Glu Arg Asn Ser Tyr Ser Cys Ser Val
385                 390                 395                 400

Val His Glu Gly Leu His Asn His His Thr Thr Lys Ser Phe Ser
                405                 410                 415

<210> SEQ ID NO 10
<211> LENGTH: 415
<212> TYPE: PRT
<213> ORGANISM: Artificial sequence
<220> FEATURE:
<223> OTHER INFORMATION: Pro-TACE, Arg58 to Ala mutated, fused to an Fc
```

-continued region, polypeptide sequence

<400> SEQUENCE: 10

Asp Pro Gly Phe Gly Pro His Gln Arg Leu Glu Lys Leu Asp Ser Leu
1               5                   10                  15

Leu Ser Asp Tyr Asp Ile Leu Ser Leu Ser Asn Ile Gln Gln His Ser
            20                  25                  30

Val Arg Lys Ala Asp Leu Gln Thr Ser Thr His Val Glu Thr Leu Leu
        35                  40                  45

Thr Phe Ser Ala Leu Lys Arg His Phe Lys Leu Tyr Leu Thr Ser Ser
    50                  55                  60

Thr Glu Arg Phe Ser Gln Asn Phe Lys Val Val Val Asp Gly Lys
65                  70                  75                  80

Asn Glu Ser Glu Tyr Thr Val Lys Trp Gln Asp Phe Phe Thr Gly His
                85                  90                  95

Val Val Gly Glu Pro Asp Ser Arg Val Leu Ala His Ile Arg Asp Asp
            100                 105                 110

Asp Val Ile Arg Ile Asn Thr Asp Gly Ala Glu Tyr Asn Ile Glu
        115                 120                 125

Pro Leu Trp Arg Phe Val Asn Asp Thr Lys Asp Lys Arg Met Leu Val
    130                 135                 140

Tyr Lys Ser Glu Asp Ile Lys Asn Val Ser Arg Leu Gln Ser Pro Lys
145                 150                 155                 160

Val Cys Gly Tyr Leu Lys Val Asp Asn Glu Glu Leu Leu Pro Lys Gly
                165                 170                 175

Leu Val Asp Arg Glu Pro Pro Glu Glu Leu Val His Arg Val Lys Arg
            180                 185                 190

Val Glu Cys Pro Pro Cys Pro Ala Pro Pro Val Ala Gly Pro Ser Val
        195                 200                 205

Phe Leu Phe Pro Pro Lys Pro Lys Asp Thr Leu Met Ile Ser Arg Thr
    210                 215                 220

Pro Glu Val Thr Cys Val Val Val Asp Val Ser His Glu Asp Pro Glu
225                 230                 235                 240

Val Gln Phe Asn Trp Tyr Val Asp Gly Met Glu Val His Asn Ala Lys
                245                 250                 255

Thr Lys Pro Arg Glu Glu Gln Phe Asn Ser Thr Phe Arg Val Val Ser
            260                 265                 270

Val Leu Thr Val Val His Gln Asp Trp Leu Asn Gly Lys Glu Tyr Lys
        275                 280                 285

Cys Ala Val Ser Asn Lys Gly Leu Pro Ala Pro Ile Glu Lys Thr Ile
    290                 295                 300

Ser Lys Thr Lys Gly Gln Pro Arg Glu Pro Gln Val Tyr Thr Leu Pro
305                 310                 315                 320

Pro Ser Arg Glu Glu Met Thr Lys Asn Gln Val Ser Leu Thr Cys Leu
                325                 330                 335

Val Lys Gly Phe Tyr Pro Ser Asp Ile Ala Val Glu Trp Glu Ser Asn
            340                 345                 350

Gly Gln Pro Glu Asn Asn Tyr Lys Thr Thr Pro Pro Met Leu Asp Ser
        355                 360                 365

Asp Gly Ser Phe Phe Leu Tyr Ser Lys Leu Thr Val Asp Lys Ser Arg
    370                 375                 380

Trp Gln Gln Gly Asn Val Phe Ser Cys Ser Val Met His Glu Ala Leu
385                 390                 395                 400

His Asn His Tyr Thr Gln Lys Ser Leu Ser Leu Ser Pro Gly Lys
            405                 410                 415

<210> SEQ ID NO 11
<211> LENGTH: 639
<212> TYPE: DNA
<213> ORGANISM: Artificial sequence
<220> FEATURE:
<223> OTHER INFORMATION: His tagged non-mutated pro-TACE coding sequence

<400> SEQUENCE: 11

```
atgggcagca gccatcatca tcatcatcac tccgcgggtg aaaacctgta cttccagggt      60
accgacccgg gctttggccc gcatcagcgt ctggaaaaac tggatagcct gctgtctgat     120
tatgatattc tgagcctgtc taacattcag cagcatagcg tgcgtaaacg tgatctgcag     180
accagcaccc atgtggaaac cctgctgacc tttagcgcgc tgaaacgtca ttttaaactg     240
tatctgacca gcagcaccga acgttttagc cagaacttta agtggtggt ggtggatggc      300
aaaaacgaaa gcaatacac cgtgaaatgg caggattttt ttaccggcca tgtggtgggc      360
gaaccggata gccgtgtgct ggcccatatt cgtgatgatg atgtgattat ccgcattaac     420
accgatggcg cggaatataa cattgaaccg ctgtggcgtt ttgtgaacga taccaaagat     480
aaacgcatgc tggtgtacaa aagcgaagat atcaaaaacg tgagccgtct gcagagcccg     540
aaagtgtgcg gctatctgaa agtggataac gaagaactgc tgccgaaagg cctggtggat     600
cgtgaaccgc cggaagaact ggtgcatcgt gtgaaacgt                            639
```

<210> SEQ ID NO 12
<211> LENGTH: 639
<212> TYPE: DNA
<213> ORGANISM: Artificial sequence
<220> FEATURE:
<223> OTHER INFORMATION: His tagged pro-TACE, Arg58 to Ala mutated,
      coding sequence

<400> SEQUENCE: 12

```
atgggcagca gccatcatca tcatcatcac tccgcgggtg aaaacctgta cttccagggt      60
accgacccgg gctttggccc gcatcagcgt ctggaaaaac tggatagcct gctgtctgat     120
tatgatattc tgagcctgtc taacattcag cagcatagcg tgcgtaaagc tgatctgcag     180
accagcaccc atgtggaaac cctgctgacc tttagcgcgc tgaaacgtca ttttaaactg     240
tatctgacca gcagcaccga acgttttagc cagaacttta agtggtggt ggtggatggc      300
aaaaacgaaa gcaatacac cgtgaaatgg caggattttt ttaccggcca tgtggtgggc      360
gaaccggata gccgtgtgct ggcccatatt cgtgatgatg atgtgattat ccgcattaac     420
accgatggcg cggaatataa cattgaaccg ctgtggcgtt ttgtgaacga taccaaagat     480
aaacgcatgc tggtgtacaa aagcgaagat atcaaaaacg tgagccgtct gcagagcccg     540
aaagtgtgcg gctatctgaa agtggataac gaagaactgc tgccgaaagg cctggtggat     600
cgtgaaccgc cggaagaact ggtgcatcgt gtgaaacgt                            639
```

<210> SEQ ID NO 13
<211> LENGTH: 639
<212> TYPE: DNA
<213> ORGANISM: Artificial sequence
<220> FEATURE:
<223> OTHER INFORMATION: His tagged pro-TACE, Arg58 to Ala, Arg211 to
      Ala and Arg214 to Gly mutated, coding sequence

<400> SEQUENCE: 13

```
atgggcagca gccatcatca tcatcatcac tccgcgggtg aaaacctgta cttccagggt    60
accgacccgg gctttggccc gcatcagcgt ctggaaaaac tggatagcct gctgtctgat   120
tatgatattc tgagcctgtc taacattcag cagcatagcg tgcgtaaagc tgatctgcag   180
accagcaccc atgtggaaac cctgctgacc tttagcgcgc tgaaacgtca ttttaaactg   240
tatctgacca gcagcaccga acgttttagc cagaacttta agtggtggt ggtggatggc   300
aaaaacgaaa gcaatacac cgtgaaatgg caggattttt ttaccggcca tgtggtgggc   360
gaaccggata gccgtgtgct ggcccatatt cgtgatgatg atgtgattat ccgcattaac   420
accgatggcg cggaatataa cattgaaccg ctgtggcgtt ttgtgaacga taccaaagat   480
aaacgcatgc tggtgtacaa agcgaagat atcaaaaacg tgagccgtct gcagagcccg   540
aaagtgtgcg gctatctgaa agtggataac gaagaactgc tgccgaaagg cctggtggat   600
cgtgaaccgc cggaagaact ggtgcatgct gtgaaaggt                          639
```

<210> SEQ ID NO 14
<211> LENGTH: 639
<212> TYPE: DNA
<213> ORGANISM: Artificial sequence
<220> FEATURE:
<223> OTHER INFORMATION: His tagged pro-TACE, Arg58 to Ala, Arg211 to
      Ala, Arg214 to Gly and Cys184 to Ala mutated, coding sequence

<400> SEQUENCE: 14

```
atgggcagca gccatcatca tcatcatcac tccgcgggtg aaaacctgta cttccagggt    60
accgacccgg gctttggccc gcatcagcgt ctggaaaaac tggatagcct gctgtctgat   120
tatgatattc tgagcctgtc taacattcag cagcatagcg tgcgtaaagc tgatctgcag   180
accagcaccc atgtggaaac cctgctgacc tttagcgcgc tgaaacgtca ttttaaactg   240
tatctgacca gcagcaccga acgttttagc cagaacttta agtggtggt ggtggatggc   300
aaaaacgaaa gcaatacac cgtgaaatgg caggattttt ttaccggcca tgtggtgggc   360
gaaccggata gccgtgtgct ggcccatatt cgtgatgatg atgtgattat ccgcattaac   420
accgatggcg cggaatataa cattgaaccg ctgtggcgtt ttgtgaacga taccaaagat   480
aaacgcatgc tggtgtacaa agcgaagat atcaaaaacg tgagccgtct gcagagcccg   540
aaagtggccg gctatctgaa agtggataac gaagaactgc tgccgaaagg cctggtggat   600
cgtgaaccgc cggaagaact ggtgcatgct gtgaaaggt                          639
```

<210> SEQ ID NO 15
<211> LENGTH: 1314
<212> TYPE: DNA
<213> ORGANISM: Artificial sequence
<220> FEATURE:
<223> OTHER INFORMATION: Non-mutated pro-TACE fused to an Fc region,
      coding sequence

<400> SEQUENCE: 15

```
atggagacag acacactcct gctatgggta ctgctgctct gggttccagg ttccactggt    60
gactctagag acccgggctt cggcccccac cagagactcg agaagcttga ttctttgctc   120
tcagactacg atattctctc tttatctaat atccagcagc attcggtaag aaaagcagat   180
ctacagactt caacacatgt agaaacacta ctaactttt cagctttgaa aaggcatttt   240
aaattatacc tgcatcaag tactgaacgt tttcacaaa atttcaaggt cgtggtggtg   300
gatggtaaaa acgaaagcga gtacactgta aaatggcagg acttcttcac tggacacgtg   360
gttggtgagc ctgactctag ggttctagcc cacataagag atgatgatgt tataatcaga   420
```

```
atcaacacag atggggccga atataacata gagccacttt ggagatttgt taatgatacc    480
aaagacaaaa gaatgttagt ttataaatct gaagatatca agaatgtttc acgtttgcag    540
tctccaaaag tgtctggtta tttaaaagtg gataatgaag agttgctccc aaaagggtta    600
gtagacagag aaccacctga agagcttgtt catcgagtga aaagaagagc tgcggcccag    660
ccggcctgca aatgcccagc acctaatctc ttgggtggac catccgtctt catcttccct    720
ccaaagatca aggatgtact catgatctcc ctgagcccca tagtcacatg tgtggtggtg    780
gatgtgagcg aggatgaccc agatgtccag atcagctggt ttgtgaacaa cgtggaagta    840
cacacagctc agacacaaac ccatagagag gattacaaca gtactctccg ggtggtcagt    900
gccctcccca tccagcacca ggactggatg agtggcaagg agttcaaatg caaggtcaac    960
aacaaagacc tccagcgcc catcgagaga accatctcaa acccaaagg gtcagtaaga     1020 gctccacagg gatatgtctt gcctccacca gaagaagaga tgactaagaa acaggtcact    1080
ctgacctgca tggtcacaga cttcatgcct gaagacattt acgtggagtg gaccaacaac    1140
gggaaaacag agctaaacta caagaacact gaaccagtcc tggactctga tggttcttac    1200
ttcatgtaca gcaagctgag agtggaaaag aagaactggg tggaaagaaa tagctactcc    1260
tgttcagtgg tccacgaggg tctgcacaat caccacacga ctaagagctt ctcc          1314

<210> SEQ ID NO 16
<211> LENGTH: 1305
<212> TYPE: DNA
<213> ORGANISM: Artificial sequence
<220> FEATURE:
<223> OTHER INFORMATION: Pro-TACE, Arg58 to Ala mutated, fused to an Fc
      region coding region

<400> SEQUENCE: 16
atggaatgga gctgggtctt tctcttcttc ctgtcagtaa ctacaggtgt ccactccgac     60
ccgggctttg gcccgcatca gcgtctggaa aaactggata gcctgctgtc tgattatgat    120
attctgagcc tgtctaacat tcagcagcat agcgtgcgta agctgatctg cagaccagc     180 acccatgtgg aaaccctgct gacctttagc gcgctgaaac gtcattttaa actgtatctg    240
accagcagca ccgaacgttt tagccagaac tttaaagtgg tggtggtgga tggcaaaaac    300
gaaagcgaat acaccgtgaa atggcaggat ttttttaccg ccatgtggt gggcgaaccg     360 gatagccgtg tgctggccca tattcgtgat gatgatgtga ttatccgcat aacaccgat    420 ggcgcggaat ataacattga accgctgtgg cgttttgtga acgataccaa agataaacgc    480
atgctggtgt acaaaagcga agatatcaaa acgtgagcc gtctgcagag cccgaaagtg    540
tgcggctatc tgaaagtgga taacgaagaa ctgctgccga aaggcctggt ggatcgtgaa    600
ccgccggaag aactggtgca tcgtgtgaaa cgtgtggagt gcccaccttg cccagcacca    660
cctgtggcag gaccttcagt cttcctcttc ccccccaaaac ccaaggacac cctgatgatc    720
tccagaaccc ctgaggtcac gtgcgtggtg gtggacgtga gccacgaaga cccgaggtc     780 cagttcaact ggtacgtgga cggcatggag gtgcataatg ccaagacaaa gccacgggag    840
gagcagttca acagcacgtt ccgtgtggtc agcgtcctca ccgtcgtgca ccaggactgg    900
ctgaacggca aggagtacaa gtgcgcggtc tccaacaaag gcctcccagc ccccatcgag    960
aaaaccatct ccaaaaccaa agggcagccc cgagaaccac aggtgtacac cctgccccca    1020
tcccgggagg agatgaccaa gaaccaggtc agcctgacct gcctggtcaa aggcttctac    1080
cccagcgaca tcgccgtgga gtgggagagc aatgggcagc cggagaacaa ctacaagacc    1140
```

```
acacctccca tgctggactc cgacggctcc ttcttcctct acagcaagct caccgtggac    1200
aagagcaggt ggcagcaggg gaacgtcttc tcatgctccg tgatgcatga ggctctgcac    1260
aaccactaca cacagaagag cctctccctg tctccgggta aatga                    1305
```

```
<210> SEQ ID NO 17
<211> LENGTH: 213
<212> TYPE: PRT
<213> ORGANISM: Artificial sequence
<220> FEATURE:
<223> OTHER INFORMATION: Non-mutated pro-TACE polypeptide
      sequence fused to a polyhistidine tag

<400> SEQUENCE: 17
```

```
Met Gly Ser Ser His His His His His Ser Ala Gly Glu Asn Leu
1               5                   10                  15

Tyr Phe Gln Gly Thr Asp Pro Gly Phe Gly Pro His Gln Arg Leu Glu
            20                  25                  30

Lys Leu Asp Ser Leu Leu Ser Asp Tyr Asp Ile Leu Ser Leu Ser Asn
        35                  40                  45

Ile Gln Gln His Ser Val Arg Lys Arg Asp Leu Gln Thr Ser Thr His
    50                  55                  60

Val Glu Thr Leu Leu Thr Phe Ser Ala Leu Lys Arg His Phe Lys Leu
65                  70                  75                  80

Tyr Leu Thr Ser Ser Thr Glu Arg Phe Ser Gln Asn Phe Lys Val Val
                85                  90                  95

Val Val Asp Gly Lys Asn Glu Ser Glu Tyr Thr Val Lys Trp Gln Asp
            100                 105                 110

Phe Phe Thr Gly His Val Val Gly Glu Pro Asp Ser Arg Val Leu Ala
        115                 120                 125

His Ile Arg Asp Asp Asp Val Ile Ile Arg Ile Asn Thr Asp Gly Ala
    130                 135                 140

Glu Tyr Asn Ile Glu Pro Leu Trp Arg Phe Val Asn Asp Thr Lys Asp
145                 150                 155                 160

Lys Arg Met Leu Val Tyr Lys Ser Glu Asp Ile Lys Asn Val Ser Arg
                165                 170                 175

Leu Gln Ser Pro Lys Val Cys Gly Tyr Leu Lys Val Asp Asn Glu Glu
            180                 185                 190

Leu Leu Pro Lys Gly Leu Val Asp Arg Glu Pro Pro Glu Glu Leu Val
        195                 200                 205

His Arg Val Lys Arg
    210
```

```
<210> SEQ ID NO 18
<211> LENGTH: 21
<212> TYPE: PRT
<213> ORGANISM: Artificial sequence
<220> FEATURE:
<223> OTHER INFORMATION: A polyhistidine tag

<400> SEQUENCE: 18
```

```
Met Gly Ser Ser His His His His His Ser Ala Gly Glu Asn Leu
1               5                   10                  15

Tyr Phe Gln Gly Thr
            20
```

```
<210> SEQ ID NO 19
<211> LENGTH: 192
```

```
<212> TYPE: PRT
<213> ORGANISM: Artificial sequence
<220> FEATURE:
<223> OTHER INFORMATION: Pro-TACE, Cys184 to Ala mutated, polypeptide
      sequence

<400> SEQUENCE: 19

Asp Pro Gly Phe Gly Pro His Gln Arg Leu Glu Lys Leu Asp Ser Leu
1               5                   10                  15

Leu Ser Asp Tyr Asp Ile Leu Ser Leu Ser Asn Ile Gln Gln His Ser
            20                  25                  30

Val Arg Lys Arg Asp Leu Gln Thr Ser Thr His Val Glu Thr Leu Leu
        35                  40                  45

Thr Phe Ser Ala Leu Lys Arg His Phe Lys Leu Tyr Leu Thr Ser Ser
    50                  55                  60

Thr Glu Arg Phe Ser Gln Asn Phe Lys Val Val Val Asp Gly Lys
65                  70                  75                  80

Asn Glu Ser Glu Tyr Thr Val Lys Trp Gln Asp Phe Phe Thr Gly His
                85                  90                  95

Val Val Gly Glu Pro Asp Ser Arg Val Leu Ala His Ile Arg Asp Asp
            100                 105                 110

Asp Val Ile Ile Arg Ile Asn Thr Asp Gly Ala Glu Tyr Asn Ile Glu
        115                 120                 125

Pro Leu Trp Arg Phe Val Asn Asp Thr Lys Asp Lys Arg Met Leu Val
    130                 135                 140

Tyr Lys Ser Glu Asp Ile Lys Asn Val Ser Arg Leu Gln Ser Pro Lys
145                 150                 155                 160

Val Ala Gly Tyr Leu Lys Val Asp Asn Glu Glu Leu Leu Pro Lys Gly
                165                 170                 175

Leu Val Asp Arg Glu Pro Pro Glu Glu Leu Val His Arg Val Lys Arg
            180                 185                 190

<210> SEQ ID NO 20
<211> LENGTH: 5
<212> TYPE: PRT
<213> ORGANISM: Artificial Sequence
<220> FEATURE:
<223> OTHER INFORMATION: Furin like serine protease recognition sequence

<400> SEQUENCE: 20

Arg Val Lys Arg Arg
1               5

<210> SEQ ID NO 21
<211> LENGTH: 5
<212> TYPE: PRT
<213> ORGANISM: Artificial Sequence
<220> FEATURE:
<223> OTHER INFORMATION: Furin like serine protease recognition sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 21

Arg Xaa Xaa Arg Xaa
1               5
```

```
<210> SEQ ID NO 22
<211> LENGTH: 4
<212> TYPE: PRT
<213> ORGANISM: Artificial Sequence
<220> FEATURE:
<223> OTHER INFORMATION: Furin like serine protease recognition sequence

<400> SEQUENCE: 22

Arg Lys Arg Asp
1

<210> SEQ ID NO 23
<211> LENGTH: 7
<212> TYPE: PRT
<213> ORGANISM: Artificial Sequence
<220> FEATURE:
<223> OTHER INFORMATION: non-canonical Furin recognition sequence

<400> SEQUENCE: 23

His Ser Val Arg Lys Arg Asp
1               5
```